US012351652B2

(12) United States Patent
Masuya et al.

(10) Patent No.: US 12,351,652 B2
(45) Date of Patent: Jul. 8, 2025

(54) HEMAGGLUTININ-BINDING PEPTIDE

(71) Applicant: PeptiDream Inc., Kawasaki (JP)

(72) Inventors: Keiichi Masuya, Kawasaki (JP); Masaki Ohuchi, Kawasaki (JP)

(73) Assignee: PeptiDream Inc., Kanagawa (JP)

( * ) Notice: Subject to any disclaimer, the term of this patent is extended or adjusted under 35 U.S.C. 154(b) by 242 days.

(21) Appl. No.: 17/432,072

(22) PCT Filed: Feb. 17, 2020

(86) PCT No.: PCT/JP2020/006146
§ 371 (c)(1),
(2) Date: Aug. 18, 2021

(87) PCT Pub. No.: WO2020/171028
PCT Pub. Date: Aug. 27, 2020

(65) Prior Publication Data

US 2024/0228544 A1 Jul. 11, 2024

(30) Foreign Application Priority Data

Feb. 18, 2019 (JP) ................................ 2019-026185

(51) Int. Cl.

| | |
|---|---|
| ***C07K 7/64*** | (2006.01) |
| ***A61K 38/00*** | (2006.01) |
| ***A61P 31/16*** | (2006.01) |
| ***G01N 33/569*** | (2006.01) |

(52) U.S. Cl.
CPC ................ *C07K 7/64* (2013.01); *A61P 31/16* (2018.01); *G01N 33/56983* (2013.01); *A61K 38/00* (2013.01); *G01N 2333/11* (2013.01); *G01N 2469/10* (2013.01)

(58) Field of Classification Search
None
See application file for complete search history.

(56) References Cited

U.S. PATENT DOCUMENTS

| | | | | |
|---|---|---|---|---|
| 2017/0333549 | A1* | 11/2017 | Kubota ................ | A61K 39/145 |
| 2019/0282688 | A1 | 9/2019 | Kubota et al. | |

FOREIGN PATENT DOCUMENTS

| | | | |
|---|---|---|---|
| JP | 2013-071904 | A | 4/2013 |
| JP | 2013-538564 | A | 10/2013 |
| WO | 2012-013979 | A1 | 2/2012 |
| WO | 2016-063969 | A1 | 4/2016 |

* cited by examiner

*Primary Examiner* — Sergio Coffa
(74) *Attorney, Agent, or Firm* — Pyprus Pte Ltd; George D. Liu

(57) ABSTRACT

[Problem to be solved] To provide a compound having markedly higher antiviral activity than iHA 100, an intermediate for producing the compound, and a medical drug, or the like, containing the high-activity compound above. [Solution] The invention relates to a hemagglutinin-binding peptide, a pharmaceutically acceptable salts, or a solvate thereof, the hemagglutinin-binding peptide being: (1) a polypeptide comprising the amino acid sequence represented by SEQ ID NO: 1 or 2: Trp-Thr-MeGly-Asp-MePhe-MePhe-Ala-MeAla-His-Tyr-Thr-Val-hydPro-Ala-Cys (SEQ ID NO: 1), Trp-Thr-MeGly-Asp-MePhe-MePhe-Ala-MeAla-His-Tyr-Thr-Val-hydPro-Ala-Cys-Lys (SEQ ID NO: 2), or the like.

12 Claims, 5 Drawing Sheets

Specification includes a Sequence Listing.

Virus : A/Nagasaki/HA-58/2009 (H1N1)

Virus : A/Duck/Penssylvania/84 (H5N2)

Fig. 2

In vitro anti-virus activity (Virus strain: A/Duck/Pennsylvania/84)

| Compounds | EC50 (μM) |
|---|---|
| iHA100 | 2.569 |
| HA119 | 0.009 |
| HA145 | 0.116 |
| HA146 | 0.005 |
| HA151 | 0.022 |
| HA152 | 0.008 |

SEQUENCE LISTING

```
<160> NUMBER OF SEQ ID NOS: 7

<210> SEQ ID NO 1
<211> LENGTH: 15
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylalanine
<220> FEATURE:
<221> NAME/KEY: MOD_RES
<222> LOCATION: (13)..(13)
<223> OTHER INFORMATION: 4-Hydroxy-L-proline

<400> SEQUENCE: 1

Trp Thr Gly Asp Phe Phe Ala Ala His Tyr Thr Val Pro Ala Cys
1               5                   10                  15
```

<210> SEQ ID NO 2
<211> LENGTH: 16
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylalanine
<220> FEATURE:
<221> NAME/KEY: MOD_RES
<222> LOCATION: (13)..(13)
<223> OTHER INFORMATION: 4-Hydroxy-L-proline

<400> SEQUENCE: 2

Trp Thr Gly Asp Phe Phe Ala Ala His Tyr Thr Val Pro Ala Cys Lys
1 5 10 15

<210> SEQ ID NO 3
<211> LENGTH: 15
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylalanine
<220> FEATURE:
<221> NAME/KEY: MOD_RES
<222> LOCATION: (13)..(13)
<223> OTHER INFORMATION: 4-Hydroxy-L-proline
<220> FEATURE:
<221> NAME/KEY: MOD_RES
<222> LOCATION: (15)..(15)
<223> OTHER INFORMATION: AMIDATION

<400> SEQUENCE: 3

Trp Thr Gly Asp Phe Phe Ala Ala His Tyr Thr Val Pro Ala Cys
1 5 10 15

<210> SEQ ID NO 4
<211> LENGTH: 16
<212> TYPE: PRT
<213> ORGANISM: Artificial Sequence
<220> FEATURE:

-continued

<223> OTHER INFORMATION: Synthesized polypeptide
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylalanine
<220> FEATURE:
<221> NAME/KEY: MOD_RES
<222> LOCATION: (13)..(13)
<223> OTHER INFORMATION: 4-Hydroxy-L-proline
<220> FEATURE:
<221> NAME/KEY: MOD_RES
<222> LOCATION: (16)..(16)
<223> OTHER INFORMATION: Lys[gamma-C(=O)n-C11H23]-NH2

<400> SEQUENCE: 4

```
Trp Thr Gly Asp Phe Phe Ala Ala His Tyr Thr Val Pro Ala Cys Lys
1               5                   10                  15
```

<210> SEQ ID NO 5
<211> LENGTH: 16
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylalanine
<220> FEATURE:
<221> NAME/KEY: MOD_RES
<222> LOCATION: (13)..(13)
<223> OTHER INFORMATION: 4-Hydroxy-L-proline
<220> FEATURE:
<221> NAME/KEY: MOD_RES
<222> LOCATION: (16)..(16)
<223> OTHER INFORMATION: Lys[gamma-C(=O)n-C9H19]-NH2

<400> SEQUENCE: 5

```
Trp Thr Gly Asp Phe Phe Ala Ala His Tyr Thr Val Pro Ala Cys Lys
1               5                   10                  15
```

<210> SEQ ID NO 6
<211> LENGTH: 15

<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylalanine
<220> FEATURE:
<221> NAME/KEY: MOD_RES
<222> LOCATION: (13)..(13)
<223> OTHER INFORMATION: 4-Hydroxy-L-proline
<220> FEATURE:
<221> NAME/KEY: MOD_RES
<222> LOCATION: (15)..(15)
<223> OTHER INFORMATION: Cys-[NHCH2CH2NHC(=O)n-C11H23]

<400> SEQUENCE: 6

```
Trp Thr Gly Asp Phe Phe Ala Ala His Tyr Thr Val Pro Ala Cys
1               5                   10                  15
```

<210> SEQ ID NO 7
<211> LENGTH: 15
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylalanine
<220> FEATURE:
<221> NAME/KEY: MOD_RES
<222> LOCATION: (13)..(13)
<223> OTHER INFORMATION: 4-Hydroxy-L-proline
<220> FEATURE:
<221> NAME/KEY: MOD_RES
<222> LOCATION: (15)..(15)
<223> OTHER INFORMATION: Cys-[NHCH2CH2NHC(=O)n-C9H19]

<400> SEQUENCE: 7

```
Trp Thr Gly Asp Phe Phe Ala Ala His Tyr Thr Val Pro Ala Cys
1               5                   10                  15
```

HEMAGGLUTININ-BINDING PEPTIDE

TECHNICAL FIELD

The present invention relates to a hemagglutinin-binding peptide having extremely high anti-influenza virus activity, a medical drug for the prevention or therapy of influenza, and a detection agent for influenza detection, etc.

BACKGROUND ART

Influenza viruses are highly infectious and pathogenic viruses, and their epidemics show widespread pathogenicity to humans as a pandemic.

Zanamivir (brand name: Relenza®), oseltamivir (brand name: Tamiflu®), peramivir (brand name: Rapiacta®), and laninamivir (brand name: Inavir®), which inhibit neuraminidase that is necessary for the release of an influenza virus, are widely used as pharmaceutical products against influenza viruses. In addition, amantadine (brand name: Symmetrel®) and flumadine (brand name: Rimantadine®), which inhibit the enucleation process of viruses, and baloxavir marboxyl (brand name: Zofluza®), which inhibits cap-dependent endonuclease, are known as pharmaceutical products. However, although the above pharmaceutical products, especially anti-influenza drugs against neuraminidase, are widely used as pharmaceutical products, drug resistance due to mutation of viruses becomes a problem.

On the other hand, hemagglutinins are known as an essential protein for an entry of an influenza virus into a host cell, and an anti-virus molecule against this target has been reported. An anti-virus molecule that targets hemagglutinins is effective against a virus that is drug resistant as an existing anti-virus drug. Therefore, an anti-virus molecule against a target molecule different from existing pharmaceutical products is also highly useful from the viewpoint of drug resistance.

As an anti-virus molecule against hemagglutinins, an antibody molecule that binds to a hemagglutinin has been reported (e.g., Patent Documents 1-3). On the other hand, while antibody pharmaceutical products have high activity, a neutralizing antibody, which are generated when an antibody pharmaceutical product is recognized as a foreign substance in vivo, may significantly reduce the titer of the drug.

Recently, a peptide molecule having a special skeleton such as an N-methyl amino acid and a D-amino acid has been reported as a new group of molecules, which not only show high binding power and biological stability, but also their molecular weight is extremely small compared to antibodies. Therefore, it is attracting attention as a group of molecules that may solve problems faced by conventional antibody pharmaceutical products (e.g., Non-Patent Documents 1-4).

We have focused on the peptide molecule having the special skeleton, and have been searching for a peptide molecule against hemagglutinins. iHA100, a peptide molecule against hemagglutinins, is an anti-influenza virus molecule that exhibits anti-virus activity even when administered intranasally, which differs greatly from its molecular weight and the usual route of antibody administration (Patent Document 4). On the other hand, there are no reports of cases of significant improvement in anti-influenza virus activity of iHA100 and the structure thereof, and the improvement of anti-influenza virus activity thereof may greatly contribute to an improvement of a drug effect.

PRIOR ART DOCUMENTS

Patent Documents

Patent Document 1: International Publication No. 2018/108086 Brochure

Patent Document 2: International Publication No. 2018/015012 Brochure

Patent Document 3: International Publication No. 2017/122087 Brochure

Patent Document 4: International Publication No. 2013/071904 Brochure

Non-Patent Document 1: Nature Reviews Drug Discovery 17, 531-533 (2018)

Non-Patent Document 2: Current opinion in chemical biology, 34, 44-52 (2016)

Non-Patent Document 3: Annual Review of Biochemistry, 83, 727-752 (2014)

Non-Patent Document 4: Chemistry, 19, 6530-6536 (2013)

SUMMARY OF THE INVENTION

Problems to be Solved by the Invention

The purpose of this invention is to provide a compound having significantly higher anti-virus activity than iHA100, an intermediate for producing the compound, and a medical drug containing the above high-activity compound, etc.

Means to Solve the Problems

The present invention is based on the finding that a newly synthesized hemagglutinin-binding peptide has remarkable activity compared to a previously known hemagglutinin-binding peptide having anti-influenza virus activity.

One of the embodiments disclosed herein relates to a hemagglutinin-binding peptide, a pharmaceutically acceptable salt thereof, or a solvate thereof (these are also referred to as peptides of the present invention).

This hemagglutinin-binding peptide is any of the following peptides (1) to (7):

(1) a polypeptide consisting of an amino acid sequence represented by the SEQ ID NO: 1 or 2:

```
                                        (SEQ ID NO: 1)
Trp-Thr-MeGly-Asp-MePhe-MePhe-Ala-MeAla-His-Tyr-

Thr-Val-hydPro-Ala-Cys,
and

                                        (SEQ ID NO: 2)
Trp-Thr-MeGly-Asp-MePhe-MePhe-Ala-MeAla-His-Tyr-

Thr-Val-hydPro-Ala-Cys-Lys;
```

(2) a polypeptide consisting of an amino acid sequence in which, in the SEQ ID NO: 1 or 2, the N-terminal Trp is chloroacetyl-Trp;

(3) a polypeptide consisting of an amino acid sequence in which, in the SEQ ID NO: 1, the N-terminal Trp is chloroacetyl-Trp and the C-terminal Cys has been modified as represented by Formula (I) via an amide bond;

(4) a polypeptide consisting of a sequence in which, in the SEQ ID NO: 2, the N-terminal Trp is chloroacetyl-Trp and the C-terminal Lys has been substituted with a modified lysine derivative represented by Formula (II);

(5) a polypeptide consisting of an amino acid sequence in which, in the SEQ ID NO: 1, the C-terminal Cys has been modified as represented by Formula (I) via an amide bond;

(6) a polypeptide consisting of a sequence including a lysine derivative represented by Formula (II) in which, in the SEQ ID NO: 2, the side chain of Lys has been modified with an acyl group; and (7) a peptide having an amino acid sequence in which, in the amino acid sequence in any of (1) to (6) above, one or two amino acids have been deleted, added, substituted, or inserted (however a sequence in which, in the SEQ ID NO: 1, the C-terminal Cys has been deleted, and a sequence in which, in the SEQ ID NO: 2, the C-terminal Lys has been deleted, are excluded).

[Formula 9]

Formula (I)

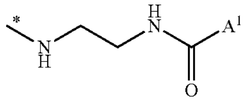

(In Formula (I), * denotes a linking moiety to a carbonyl group of the C-terminal Cys, and $A^1$ denotes a $C_8$-$C_{12}$ alkyl group.)

[Formula 10]

Formula (II)

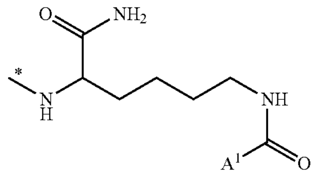

(In Formula (II), * denotes a linking moiety to a carbonyl group of the C-terminal Cys, and $A^1$ denotes a $C_8$-$C_{12}$ alkyl group.)

Preferred examples of the hemagglutinin-binding peptide are as follows:

(1) the polypeptide consisting of the amino acid sequence represented by the SEQ ID NO: 1 or 2;

(5) the polypeptide consisting of the amino acid sequence in which, in the SEQ ID NO: 1, the C-terminal Cys has been modified as represented by Formula (I) via an amide bond;

(6) a polypeptide consisting of a sequence in which, in the SEQ ID NO: 2, the C-terminal Lys has been substituted with a modified lysine derivative represented by Formula (II); or (7) a peptide having an amino acid sequence in which, in the amino acid sequence in any of (1), (5) and (6) above, one or two amino acids have been deleted, added, substituted, or inserted (however the sequence in which, in the SEQ ID NO: 1, the C-terminal Cys has been deleted, and the sequence in which, in the SEQ ID NO: 2, the C-terminal Lys has been deleted, are excluded).

A preferred example of the hemagglutinin-binding peptide is one in which the hemagglutinin-binding peptide is cyclic.

A preferred example of the hemagglutinin-binding peptide is one represented by formula (III) or (IV) below.

[Formula 11]

(III)

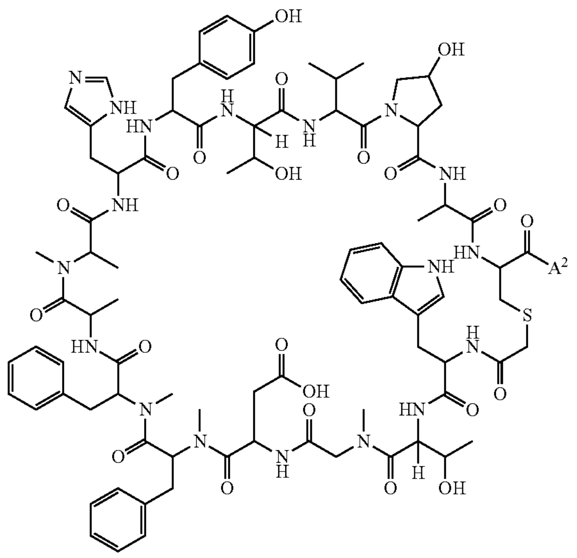

(In Formula (III), Formula $A^2$ denotes a group represented by —$NH_2$ or a group represented by Formula (I).)

[Formula 12]

(IV)

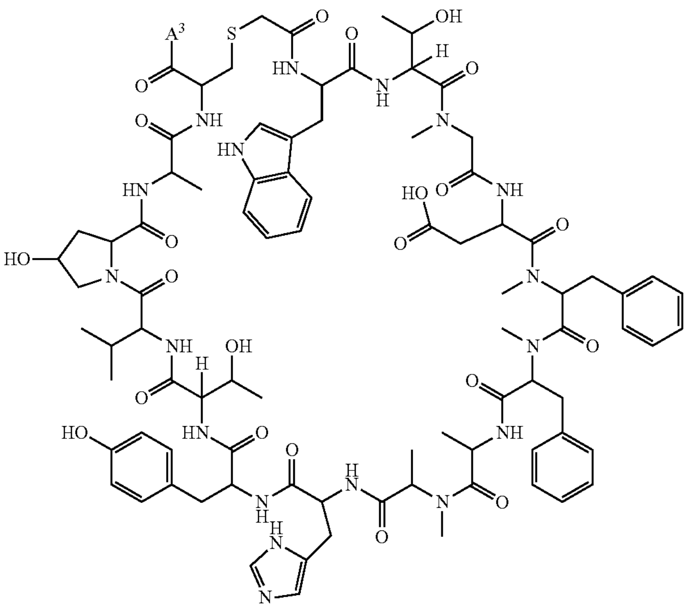

(In Formula (IV), Formula $A^3$ denotes a group represented by —$NH_2$ or a group represented by Formula (II).)

A preferred example of the hemagglutinin-binding peptide other than the above is represented by formula (V) or (VI) below.

[Formula 13]

(V)

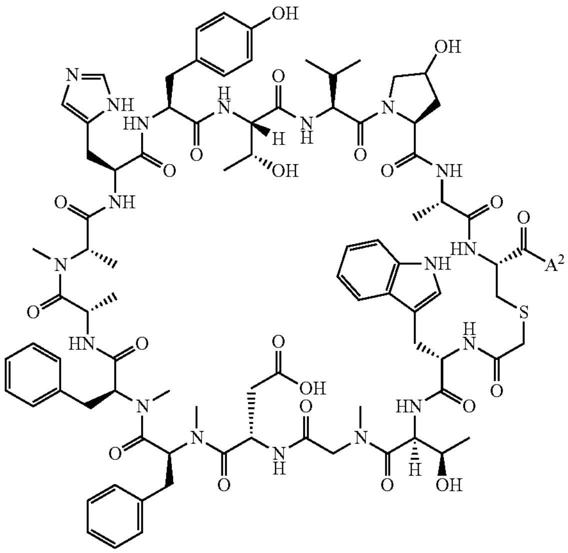

(In Formula (V), Formula A denotes a group represented by —$NH_2$ or a group represented by Formula (IIa).)

[Formula 14]

(IIa)

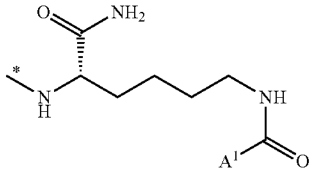

(In Formula (IIa), * denotes a linking moiety, and $A^1$ denotes a $C_8$-$C_{12}$ alkyl group.)

[Formula 15]

(VI)

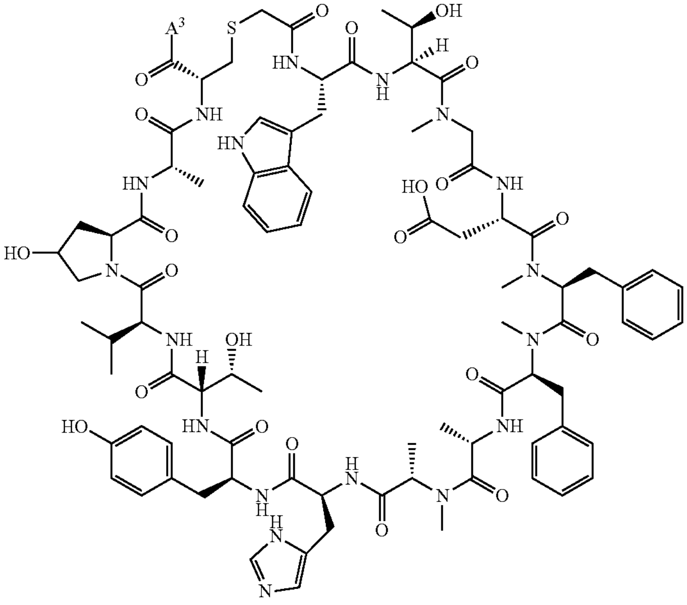

In Formula (VI), Formula $A^5$ denotes a group represented by $-NH_2$ or a group represented by Formula (I).

A preferred example of the hemagglutinin-binding peptide other than the above is represented by formula (VII) below.

[Formula 16]

(VII)

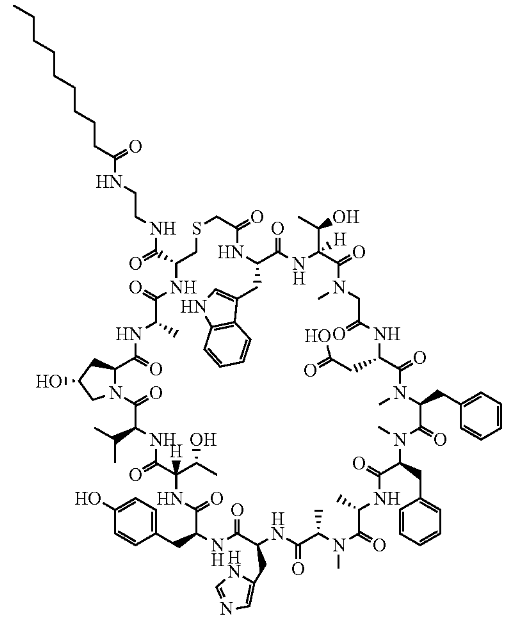

An aspect in this description other than the above is a medical drug for the prevention of virus infection or for the therapy of a virus infectious disease including any of the above-mentioned hemagglutinin-binding peptide, pharmaceutically acceptable salt thereof, or solvate thereof. Yet another aspect is a medical drug for the prevention or therapy of influenza (a prophylactic agent or therapeutic agent, a pharmaceutical product for influenza) including any of the above-mentioned hemagglutinin-binding peptide, pharmaceutically acceptable salt thereof, or solvate thereof.

Another embodiment disclosed in this description relates to a virus detection agent. Yet another aspect relates to an influenza virus detection agent. This virus detection agent contains the above-mentioned hemagglutinin-binding peptide.

Another embodiment disclosed in this description relates to a kit for virus detection contains the above-mentioned virus detection agent.

Effects of the Invention

As shown by the examples, this application may provide a peptide having significantly higher anti-influenza virus activity than iHA100, a medical drug for the prevention or therapy of influenza and an influenza virus detection agent using the peptide, and an intermediate for synthesizing the above-mentioned peptide.

BRIEF DESCRIPTION OF THE DRAWINGS

FIG. 1 (B) are graphs showing evaluation results of in vitro anti-influenza virus activity of iHA100 and HA152 using influenza virus A/Puerto Rico/8/34 (H1N1).

FIG. 1 (C) are graphs showing evaluation results of in vitro anti-influenza virus activity of iHA100 and HA152 using influenza virus A/Duck/Pennsylvania/84 (H5N2).

FIG. 2 is a table showing results of in vitro anti-influenza virus activity for iHA100, and HA119, HA145, HA146, HA151, HA152 using influenza virus A/Duck/Pennsylvania/84 (H5N2) as EC50 value.

DETAILED DESCRIPTION

Figure 1A:
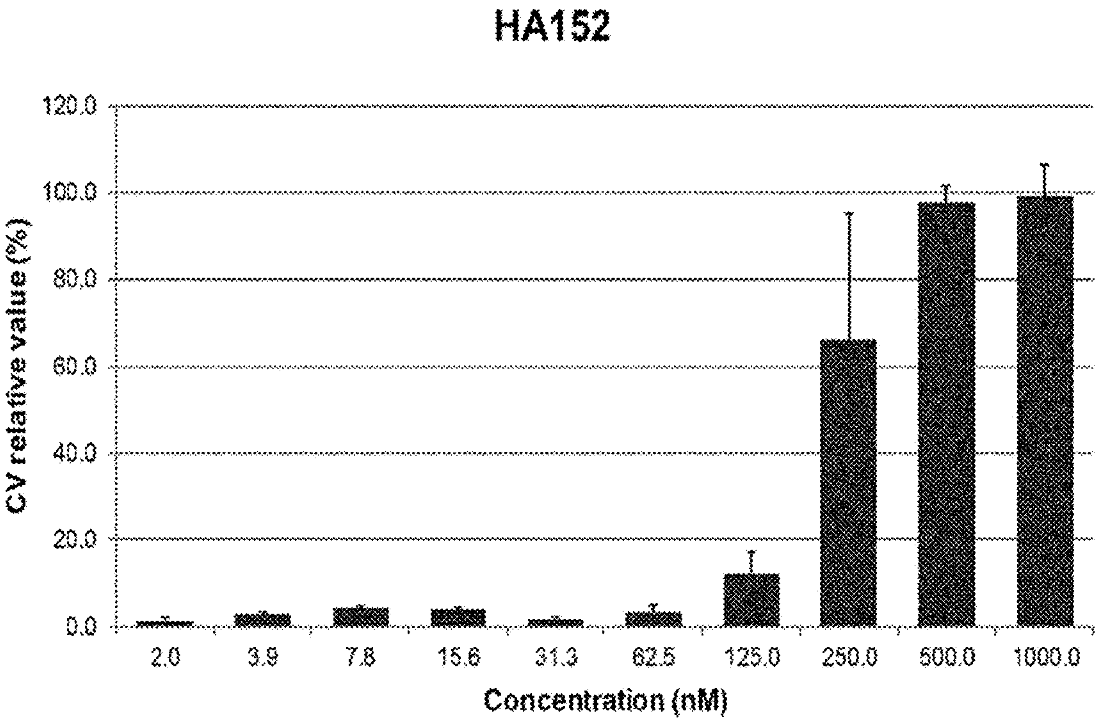
FIG. 1 (A) are graphs showing evaluation results of in vitro anti-influenza virus activity of iHA100 and HA152 using influenza virus A/Nagasaki/HA-58/2009 (H1N1).
Figure 1A:
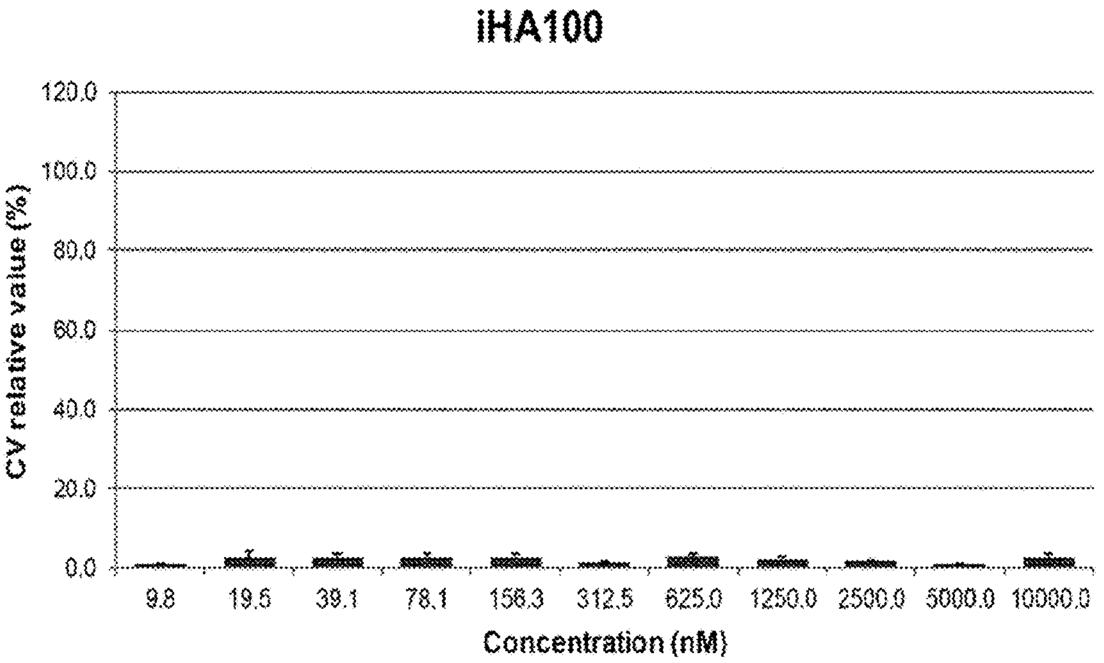
Figure 1B:
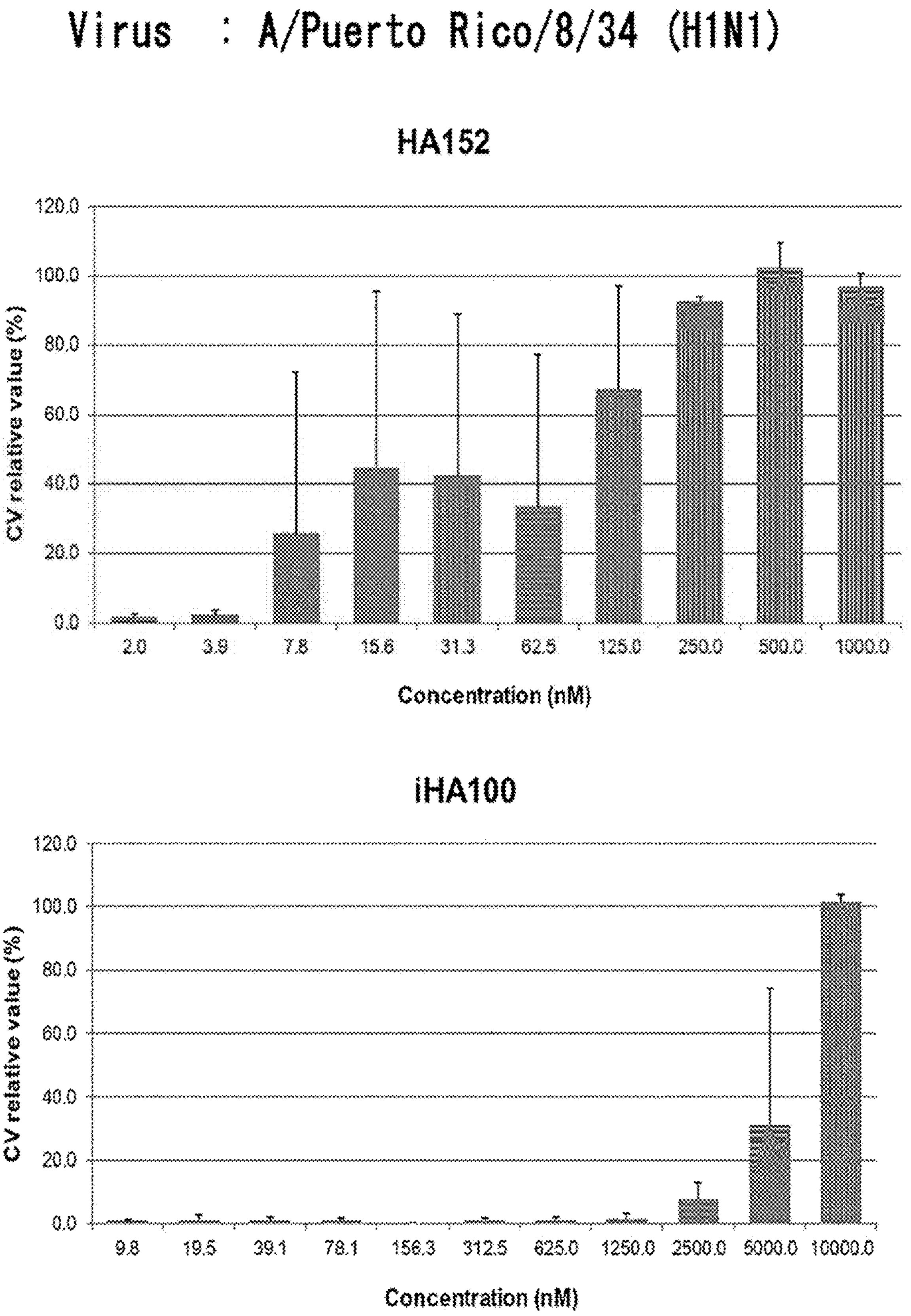
Figure 1C:
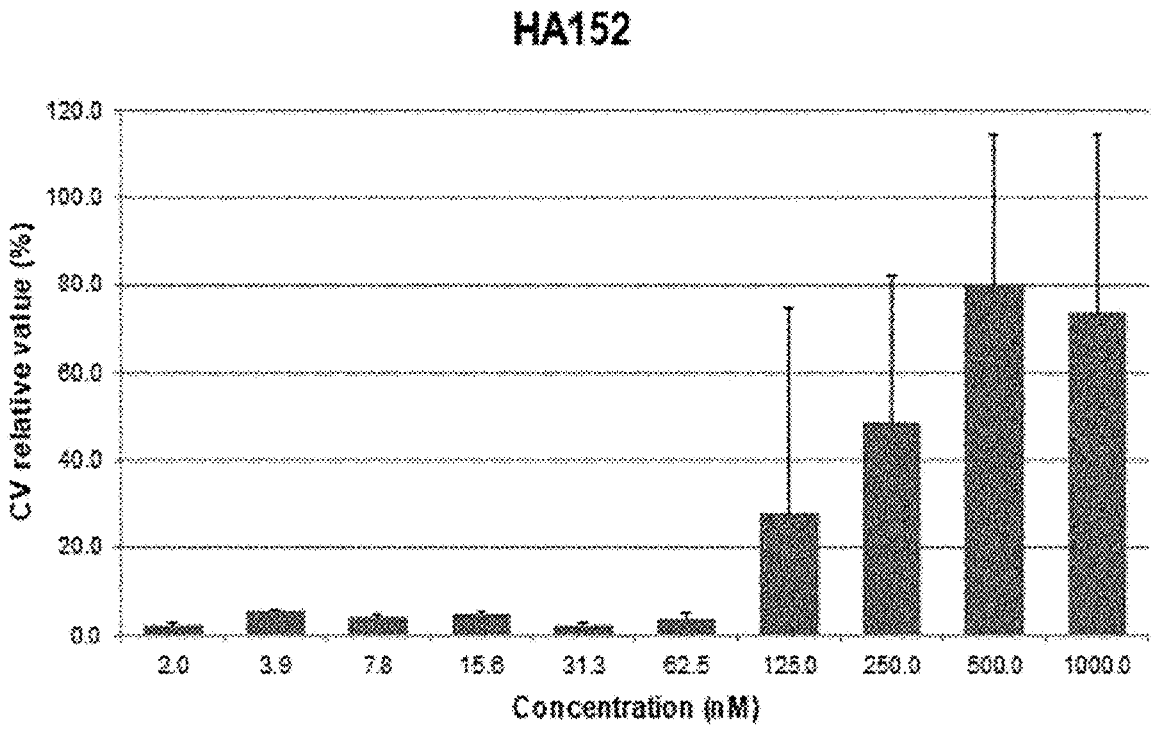
Figure 1C:
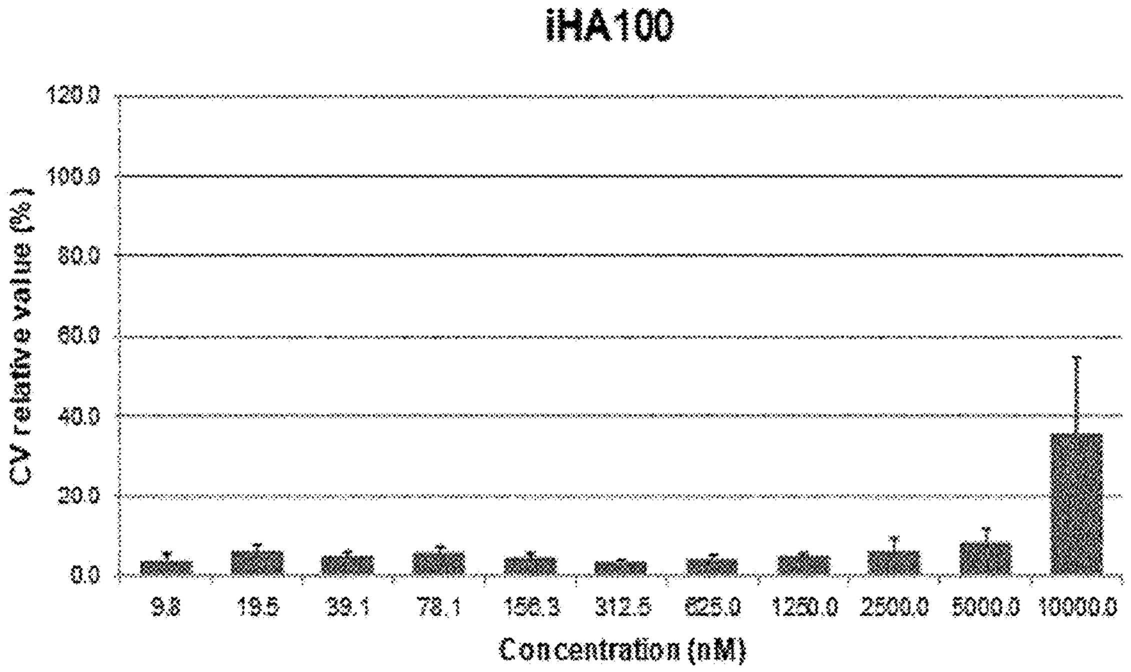

Embodiments to carry out the present invention will be described below. The present invention is not limited to the embodiments described below, and includes those appropriately modified by those skilled in the art from the following embodiments to the extent obvious.

One of the embodiments disclosed herein relates to a hemagglutinin-binding peptide, a hemagglutinin-binding peptide, a pharmaceutically acceptable salt thereof, or a solvate thereof.

Herein, the hemagglutinin means an antigenic glycoprotein present on the surface of many bacteria and viruses, including influenza viruses, and is denoted as "HA". The hemagglutinin is involved in a process of virus adhesion to a host cell. Specifically, when the hemagglutinin on the surface of the virus binds to a sialic acid on the surface of the target host cell, the virus is enveloped by a cell membrane and taken up into the cell in the form of a virus-containing endosome. Subsequently, an endosomal membrane and a virus membrane fuse, a virus genome is inserted into the cell, and proliferation begins.

Influenza viruses are classified into three types, type A, type B, and type C. There are at least 16 subtypes of hemagglutinins in influenza virus A type that are particularly prone to pandemics, and they are referred to as H1 to H16. H1, H2, H5, H6, H8, H9, H11, H12, H13, H16, H17, H18 are referred to as Group I, and the other hemagglutinins (H3, H4, H7, H10, H14, H15) are referred to as Group II. The H in the subtype name of influenza indicates the hemagglutinin.

The hemagglutinin-binding peptide means a peptide that may bind to the hemagglutinin. Whether or not it may bind to the hemagglutinin may be confirmed according to a method known to those skilled in the art.

The pharmaceutically acceptable salt thereof means a pharmaceutically acceptable salt of the hemagglutinin-binding peptide. Examples of the salt include addition salts of inorganic acids (hydrochloric acid, hydrobromic acid, hydriodic acid, sulfuric acid, phosphoric acid, etc.), addition salts of organic acids (p-toluene sulfonic acid, methane sulfonic acid, oxalic acid, p-bromophenyl sulfonic acid, carboxylic acid, succinic acid, citric acid, benzoic acid, acetic acid, etc.), inorganic bases (ammonium hydroxide, or alkaline or alkaline earth metal hydroxides, carbonates, bicarbonates, etc.), addition salts of amino acids.

The pharmaceutically acceptable solvate thereof means a pharmaceutically acceptable solvate of the hemagglutinin-binding peptide, or a pharmaceutically acceptable solvate of the hemagglutinin-binding peptide salt. A Solvent molecule may be coordinated to the compound or the salt thereof, and examples of the solvate are hydrates and alcoholates.

This hemagglutinin-binding peptide is any of the following peptides (1) to (7):

(1) a polypeptide consisting of an amino acid sequence represented by the SEQ ID NO: 1 or 2:

```
                                       (SEQ ID NO: 1)
Trp-Thr-MeGly-Asp-MePhe-MePhe-Ala-MeAla-His-Tyr-

Thr-Val-hydPro-Ala-Cys,
and
```

-continued

```
                                       (SEQ ID NO: 2)
Trp-Thr-MeGly-Asp-MePhe-MePhe-Ala-MeAla-His-Tyr-

Thr-Val-hydPro-Ala-Cys-Lys;
```

(2) a polypeptide consisting of an amino acid sequence in which, in the SEQ ID NO: 1 or 2, the N-terminal Trp is chloroacetyl-Trp;

(3) a polypeptide consisting of an amino acid sequence in which, in the SEQ ID NO: 1, the N-terminal Trp is chloroacetyl-Trp and the C-terminal Cys has been modified as represented by Formula (I) via an amide bond;

(4) a polypeptide consisting of a sequence in which, in the SEQ ID NO: 2, the N-terminal Trp is chloroacetyl-Trp and the C-terminal Lys has been substituted with a modified lysine derivative represented by Formula (II);

(5) a polypeptide consisting of an amino acid sequence in which, in the SEQ ID NO: 1, the C-terminal Cys has been modified as represented by Formula (I) via an amide bond;

(6) a polypeptide consisting of a sequence including a lysine derivative represented by Formula (II) in which, in the SEQ ID NO: 2, the side chain of Lys has been modified with an acyl group; and (7) a peptide having an amino acid sequence in which, in the amino acid sequence in any of (1) to (6) above, one or two amino acids have been deleted, added, substituted, or inserted (however a sequence in which, in the SEQ ID NO: 1, the C-terminal Cys has been deleted, and a sequence in which, in the SEQ ID NO: 2, the C-terminal Lys has been deleted, are excluded).

[Formula 17]

Formula (I)

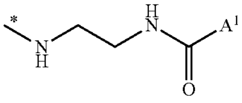

(In Formula (I), * denotes a linking moiety to a carbonyl group of the C-terminal Cys, and $A^1$ denotes a $C_8$-$C_{12}$ alkyl group.) The $C_8$-$C_{12}$ alkyl group is an alkyl group with 8-12 carbons. The $C_8$-$C_{12}$ alkyl group may be a linear alkyl group or a branched alkyl group. The $C_8$-$C_{12}$ alkyl group may be any of $C_8$ alkyl group, $C_9$ alkyl group, $C_{10}$ alkyl group, $C_{11}$ alkyl group, and $C_{12}$ alkyl group. The same applies to $A^1$ in each of the following groups.

[Formula 18]

Formula (II)

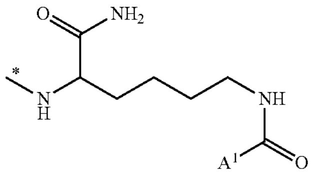

(In Formula (II), * denotes a linking moiety to a carbonyl group of the C-terminal Cys, and $A^1$ denotes a $C_8$-$C_{12}$ alkyl group.)

Preferred examples of the hemagglutinin-binding peptide are as follows:

(1) the polypeptide consisting of the amino acid sequence represented by the SEQ ID NO: 1 or 2;

(5) the polypeptide consisting of the amino acid sequence in which, in the SEQ ID NO: 1, the C-terminal Cys has been modified as represented by Formula (I) via an amide bond;

(6) a polypeptide consisting of a sequence in which, in the SEQ ID NO: 2, the C-terminal Lys has been substituted with a modified lysine derivative represented by Formula (II); or (7) a peptide having an amino acid sequence in which, in the amino acid sequence in any of (1), (5) and (6) above, one or two amino acids have been deleted, added, substituted, or inserted (however the sequence in which, in the SEQ ID NO: 1, the C-terminal Cys has been deleted, and the sequence in which, in the SEQ ID NO: 2, the C-terminal Lys has been deleted, are excluded).

Examples of a specific amino acid sequence of this peptide is as follows.

(SEQ ID NO:: 3)
Chloroacetyl-Trp-Thr-MeGly-Asp-MePhe-MePhe-Ala-MeAla-His-Tyr-Thr-Val-hydPro-Ala-Cys-$NH_2$ (SEQ ID NO:: 4)
Chloroacetyl-Trp-Thr-MeGly-Asp-MePhe-MePhe-Ala-MeAla-His-Tyr-Thr-Val-hydPro-Ala-Cys-Lys[gamma-C(=O)$n$—$C_{11}H_{23}$]—$NH_2$ (SEQ ID NO:: 5)
Chloroacetyl-Trp-Thr-MeGly-Asp-MePhe-MePhe-Ala-MeAla-His-Tyr-Thr-Val-hydPro-Ala-Cys-Lys[gamma-C(=O)$n$—$C_9H_{19}$]—$NH_2$ (SEQ ID NO:: 6)
Chloroacetyl-Trp-Thr-MeGly-Asp-MePhe-MePhe-Ala-MeAla-His-Tyr-Thr-Val-hydPro-Ala-Cys-[$NHCH_2CH_2NHC$(=O)$n$—$C_{11}H_{23}$]

(SEQ ID NO:: 7)
Chloroacetyl-Trp-Thr-MeGly-Asp-MePhe-MePhe-Ala-MeAla-His-Tyr-Thr-Val-hydPro-Ala-Cys-[$NHCH_2CH_2NHC$(=O)$n$—$C_9H_{19}$]

Herein, the amino acid (proteinogenic amino acid) residues that comprise the peptides and the polypeptides of the present invention, as well as comprise proteins, are denoted using three-letter or single-letter notations accepted by the industry.

Another amino acid disclosed herein includes amino acids that do not comprise proteins (also referred to as a non-proteinogenic amino acid, or simply a non-natural amino acid), or chemically synthesized compounds having properties known in the industry that are characteristic of amino acids. Examples of the non-natural amino acid include, but are not limited to, α,α-disubstituted amino acids (e.g., α-methyl alanine), N-alkyl-α-amino acids, N-alkyl-α-D-amino acids, β-amino acids, whose main chain structure differs from the natural type, and amino acids whose side chain structure differs from the natural type (e.g., norleucine, homohistidine, and hydroxyproline).

As examples of the non-natural amino acid disclosed herein, N-methyl glycine, a type of N-methyl amino acid that is an N-alkyl-α-amino acid, may be denoted as MeGly, N-methyl alanine as MeAla, and N-methyl phenylalanine as MePhe. In addition, as an example of the amino acid whose side chain structure differs from the natural type, 4R-hydroxyproline may be denoted as hydPro.

Chloroacetyl—means chloroacetylation, and Chloroacetyl-Trp denotes chloroacetyl-Trp.

Herein, the polypeptide means one in which two or more amino acids are bonded by a peptide bond, for example, may be one in which 8-30 amino acids are bonded by peptide bonds, and may be linear or cyclic. The polypeptide herein is preferably a cyclic amino acid of 15 or 16 amino acids.

In addition, the hemagglutinin-binding peptides according to the present invention may be cyclized (macrocyclized). Herein, the cyclization means that within a peptide, two amino acids separated by one or more amino acids are bonded directly or indirectly via a linker, etc. to make a cyclic structure within the molecule.

The cyclization may be carried out by a known method, for example, according to the method described in International Publication WO2016/063969 brochure.

A preferred example of the hemagglutinin-binding peptide is one represented by formula (III) or (IV) below.

[Formula 19]

(III)

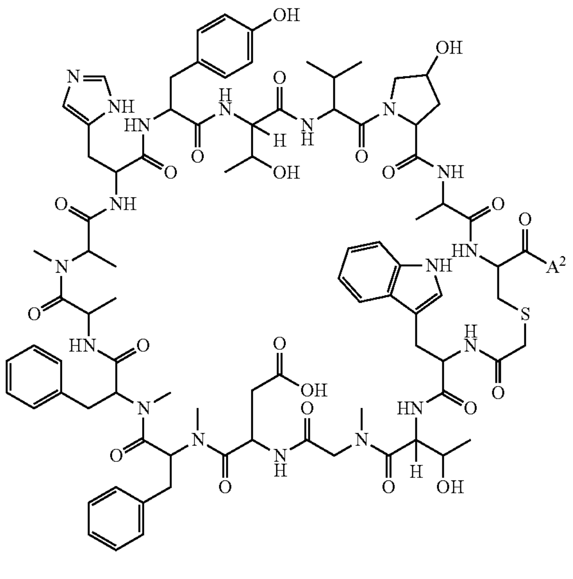

(In Formula (III), Formula $A^2$ denotes a group represented by —$NH_2$ or a group represented by Formula (I).)

[Formula 20]

(IV)

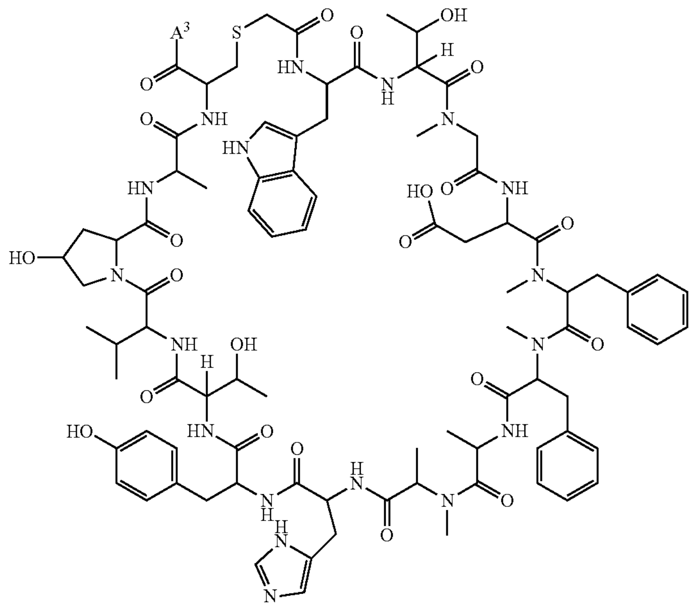

(In Formula (IV), Formula $A^3$ denotes a group represented by —$NH_2$ or a group represented by Formula (II).)

A preferred example of the hemagglutinin-binding peptide other than the above is represented by formula (V) or (VI) below.

[Formula 21]

(V)

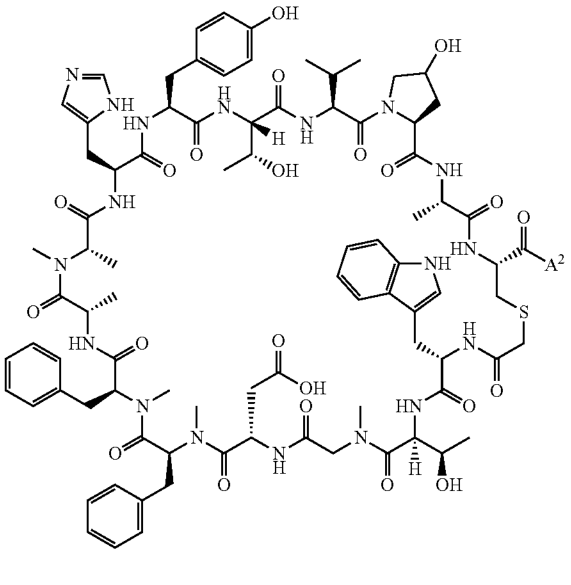

(In Formula (V), Formula $A^4$ denotes a group represented by —$NH_2$ or a group represented by Formula (IIa).)

[Formula 22]

(IIa)

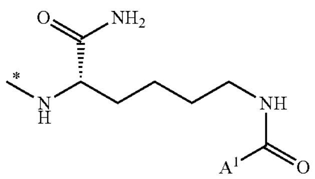

(In Formula (IIa), * denotes a linking moiety, and $A^1$ denotes a $C_8$-$C_{12}$ alkyl group.)

[Formula 23]

(VI)

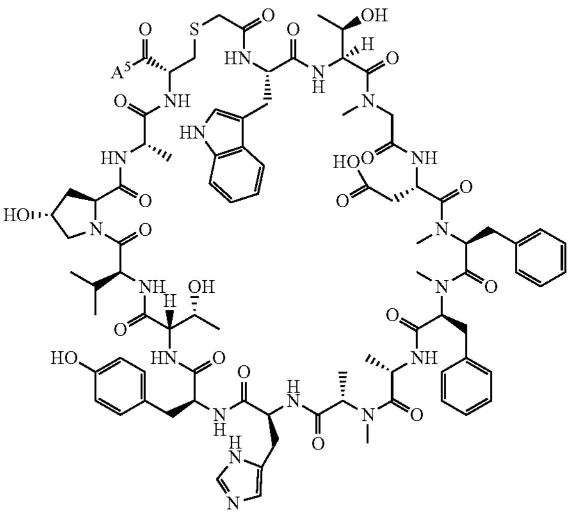

In Formula (VI), Formula $A^5$ denotes a group represented by —$NH_2$ or a group represented by Formula (I).
A preferred example of the hemagglutinin-binding peptide other than the above is represented by formula (VII) below.
[Formula 24]
(VII)
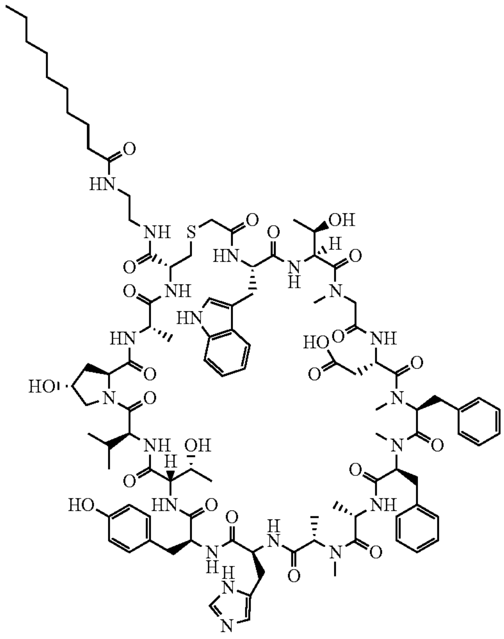
Specific structures of the cyclic peptide are as follows.
[Formula 25]
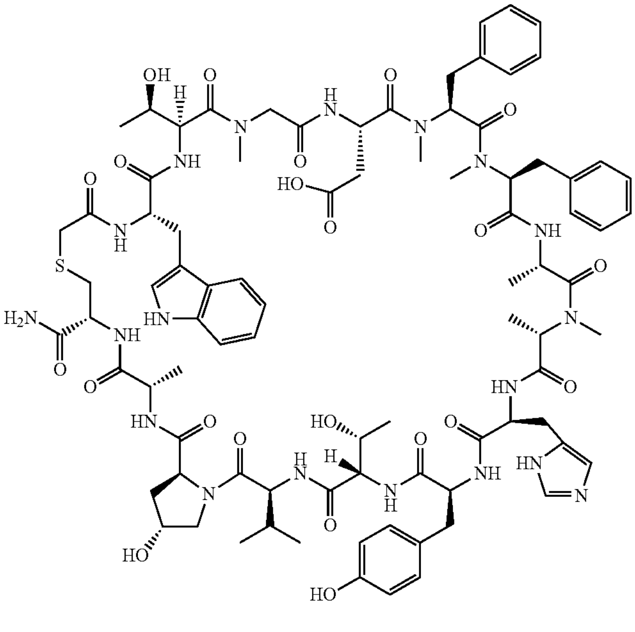

-continued
[Formula 26]
(HA145)
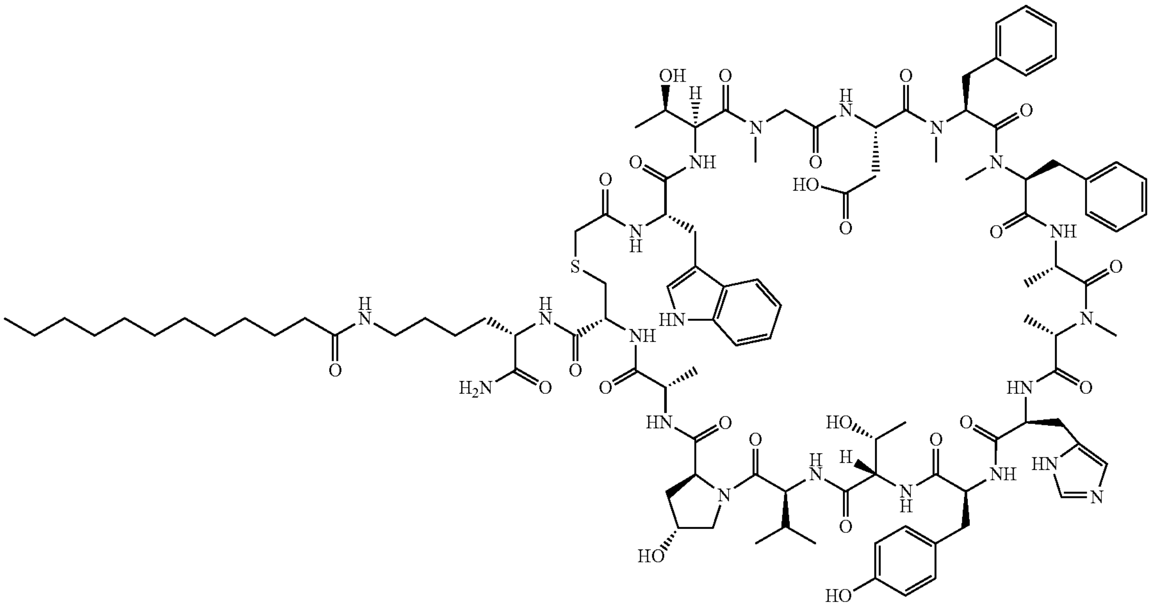
[Formula 27]
(HA146)
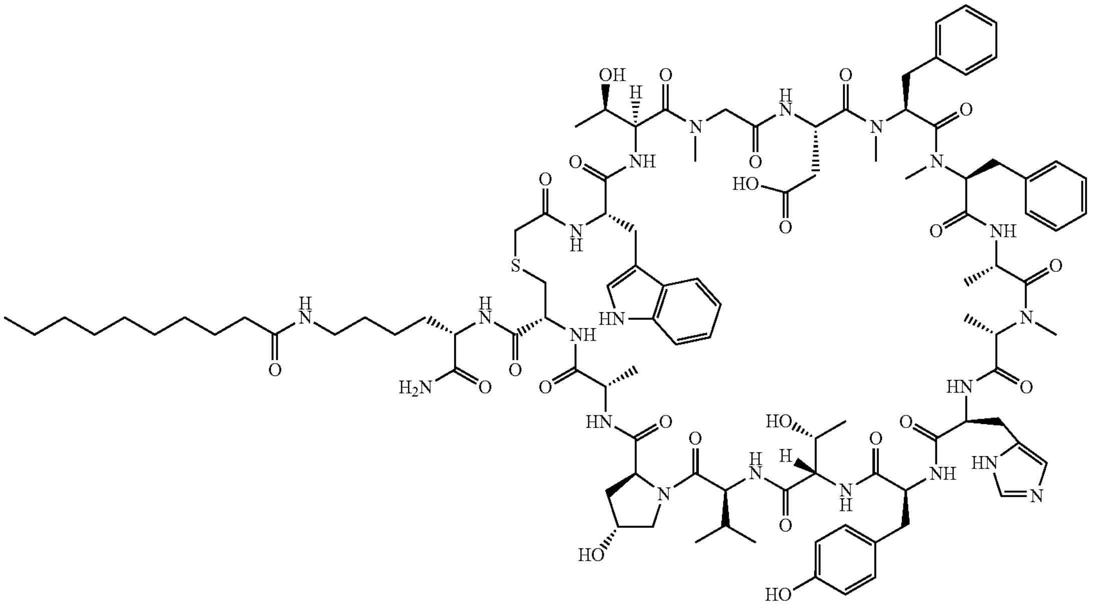

-continued

[Formula 28]

(HA151)

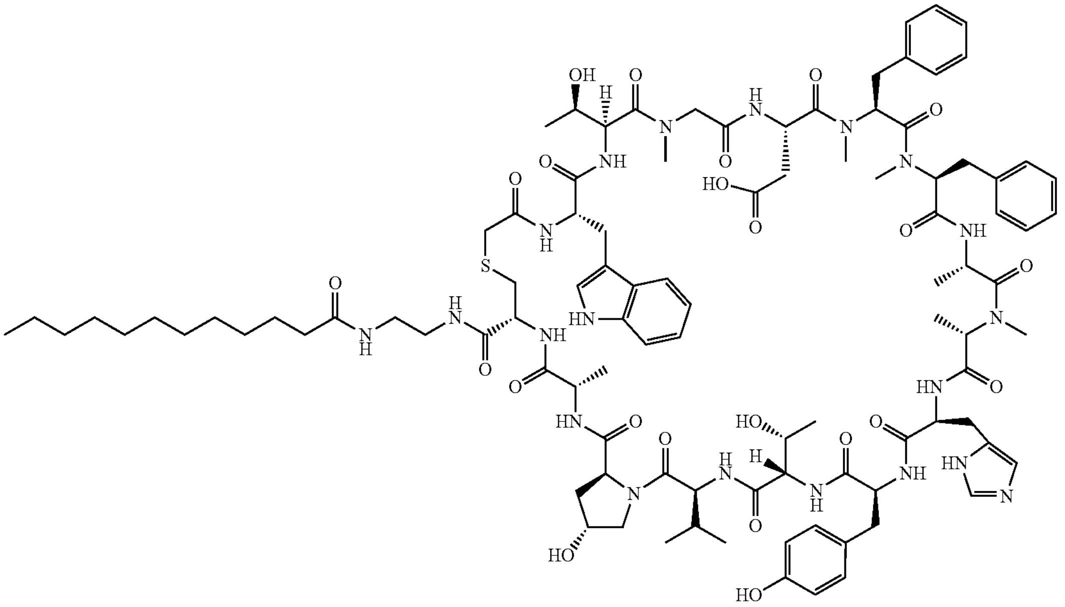

[Formula 29]

(HA152)

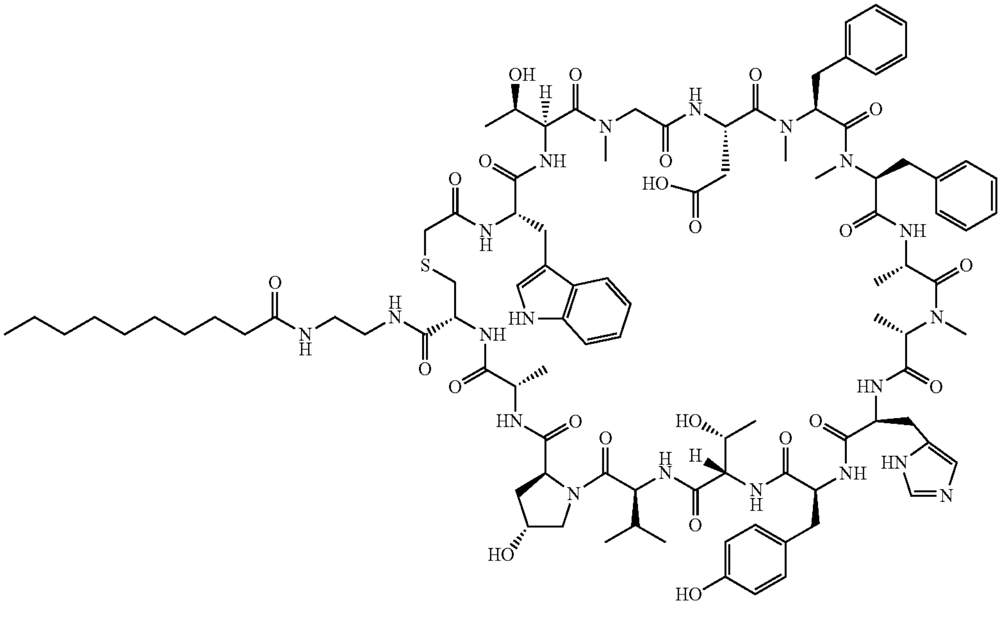

The peptides of the present invention may be produced by known methods of peptide production such as chemical synthesis methods including liquid-phase methods, solid-phase methods, and hybrid methods combining the liquid-phase and the solid-phase methods; and genetic recombination methods.

The solid phase method is, for example, an esterification reaction between a hydroxyl group of a resin having the hydroxyl group and a carboxy group of the first amino acid (usually, the C-terminal amino acid of the target peptide) whose α-amino group is protected by a protecting group. As esterification catalysts, known dehydration and condensation agents such as 1-mesitylene sulfonyl-3-nitro-1,2,4-triazole (MSNT), dicyclohexylcarbodiimide (DCC), and diisopropylcarbodiimide (DIPCDI) may be used.

Next, the protecting group of the α-amino group of the first amino acid is removed, and the second amino acid, in which all functional groups except the carboxy group of the main chain are protected, is added to activate said carboxy group, and the first and second amino acids are bonded. Furthermore, the α-amino group of the second amino acid is deprotected, and the third amino acid, in which all functional groups except the carboxy group of the main chain are protected, is added to activate said carboxy group, and the second and third amino acids are bonded. This process is repeated until a peptide of the desired length is synthesized, and then all functional groups are deprotected.

The resin used in the solid phase method includes Merrifield resin, MBHA resin, Cl-Trt resin, SASRIN resin, Wang resin, Rink amide resin, HMFS resin, Amino-PEGA resin (Merck), HMPA-PEGA resin (Merck). These resins may be washed with solvents (dimethylformamide (DMF), 2-propanol, methylene chloride, etc.) before use.

The protecting groups for the α-amino group include, but are not limited to, for example, benzyloxy carbonyl (Cbz or Z) group, tert-butoxy carbonyl (Boc) group, fluorenyl methoxycarbonyl (Fmoc) group, benzyl group, allyl group, and allyloxy carbonyl (Alloc) group, as long as they are known protecting groups. The Cbz group may be deprotected by hydrofluoric acid, hydrogenation, etc., the Boc group may be deprotected by trifluoroacetic acid (TFA), and the Fmoc group may be deprotected by a treatment with piperidine.

The protecting groups for the α-carboxy group include, but are not limited to, for example, methyl ester, ethyl ester, benzyl ester, tert-butyl ester, cyclohexyl ester, as long as they are known protecting groups.

As other functional groups of amino acids, for example, the hydroxy group of serine and threonine may be protected by benzyl group or tert-butyl group, and the hydroxy group of tyrosine is protected by 2-bromobenzyloxycarbonyl group or tert-butyl group, but not particularly limited. The amino group of the side chain of lysine, and the carboxy group of glutamic acid and aspartic acid may be protected in the same way as the α-amino group and α-carboxy group.

Activation of the carboxy group may be carried out using a condensing agent. The condensing agents include, for example, dicyclohexylcarbodiimide (DCC), diisopropylcarbodiimide (DIPCDI), 1-ethyl-3-(3-dimethylaminopropyl) carbodiimide (EDC or WSC), (1H-benzotriazol-1-yloxy)tris (dimethyl amino)phosphonium hexafluorophosphate (BOP), 1-[bis(dimethyl amino)methyl]-1H-benzotriazolium-3-oxide hexafluorophosphate (HBTU).

A cleavage of the peptide chain from the resin may be carried out by a treatment with an acid such as TFA, hydrogen fluoride (HF).

The production of peptides by the genetic recombination method (a translation synthesis system) may be carried out using a nucleic acid encoding the peptides of the present invention. The nucleic acid encoding the peptides of the present invention may be DNA or RNA.

The nucleic acid encoding the peptides of the present invention may be prepared by a known method or a method similar thereto. For example, it may be synthesized by an automatic synthesis apparatus. A restriction enzyme recognition site may be added to insert the resulting DNA into a vector, or a base sequence encoding an amino acid sequence may be incorporated to cut out the resulting peptide chains by an enzyme, etc.

As mentioned above, when the peptide of the present invention is fused with a membrane permeable peptide, etc., the above nucleic acid includes a nucleic acid encoding the membrane permeable peptide.

In order to inhibit degradation by a host-derived protease, a chimeric protein expression method may be used in which a target peptide is expressed as a chimeric peptide with another peptide. In this case, a nucleic acid that encodes the target peptide and a peptide that binds to this, is used as the above nucleic acid.

Subsequently, an expression vector is prepared using the nucleic acid encoding the peptides of the present invention. The nucleic acid may be inserted into the downstream of a promoter of the expression vector, either as is, or by digesting it with a restriction enzyme, or adding a linker, etc. The vectors include *E. coli*-derived plasmids (pBR322, pBR325, pUC12, pUC13, pUC18, pUC19, pUC118, pBluescript II, etc.), *Bacillus subtilis*-derived plasmids (PUB110, pTP5, pC1912, pTP4, pE194, pC194, etc.), yeast-derived plasmids (pSH19, pSH15, YEp, YRp, YIp, YAC, etc.), bacteriophages (ePhage, M13 Phage, etc.), viruses (retrovirus, vaccinia virus, adenovirus, adeno-associated virus (AAV), cauliflower mosaic virus, tobacco mosaic virus, baculovirus, etc.), cosmid.

The promoter may be appropriately selected depending on the type of host. If the host is an animal cell, for example, SV40 (simian virus 40)-derived promoter or CMV (cytomegalovirus)-derived promoter may be used. If the host is *E. coli*, trp promoter, T7 promoter, lac promoter, etc. may be used.

Nucleic acids encoding DNA replication start sites (ori), selection markers (antibiotic resistance, nutritional requirement, etc.) enhancers, splicing signals, poly(A)-addition signals, tags (FLAG, HA, GST, GFP, etc.), etc. may also be incorporated into the expression vector.

Next, an appropriate host cell is transformed with the above expression vector. The host may be appropriately selected in relation to the vector, for example, *E. coli, Bacillus subtilis, Bacillus* sp.), yeast, insect or insect cells, animal cells, etc. are used. For example, HEK293T cells, CHO cells, COS cells, myeloma cells, Hela cells, and Vero cells may be used as the animal cell. Transformation may be carried out according to known methods such as lipofection methods, calcium phosphate methods, electroporation methods, microinjection methods, particle gun methods, depending on the type of host. The target peptide is expressed by culturing the transformant according to the usual method.

Purification of the peptides from the transformant culture includes collecting the cultured cells, suspending them in an appropriate buffer solution, then destroying the cells by methods such as sonication, freeze-thawing, and obtaining a crude extract by centrifugation or filtration. If the peptide is secreted into the culture medium, the supernatant is collected.

Purification from the crude extract or the culture supernatant may also be carried out by known methods or methods similar thereto (e.g., salting out, dialysis methods, ultrafiltration methods, gel filtration methods, SDS-PAGE methods, ion exchange chromatography, affinity chromatography, and reverse phase high performance liquid chromatography).

The resulting peptide may be converted from an educt to a salt or from a salt to an educt by a known method or a method similar thereto.

The translation synthesis system may be a cell-free translation system. The cell-free translation system includes, for example, ribosomal proteins, aminoacyl-tRNA synthetase (ARS), ribosomal RNA, amino acids, GTP, rRNA, ATP, translation initiation factors (IF), elongation factors (EF), release factors (RF), and ribosomal regeneration factors (RRF), as well as other factors required for translation. *E. coli* extract and wheat germ extract may be added to increase the efficiency of expression. In addition, rabbit red blood cell extract or insect cell extract may be added.

Several hundred μg to several mg/mL of the peptide may be produced by continuously supplying energy to the system containing these peptides using dialysis. The system may include RNA polymerase to carry out transcription from genetic DNA as well. As commercially available cell-free translation systems, RTS-100 (registered trademark) from Roche Diagnostics, PURESYSTEM from Gene Frontier, and PURExpress In Vitro Protein Synthesis Kit from NEW ENGLAND Biolabs, etc. may be used as a system derived from *E. coli*, and those of Zoigene and CellFree Sciences may be used as a system using wheat germ extract.

According to the cell-free translation system, the expression product may be obtained in a highly pure form without purification.

In the cell-free translation system, instead of aminoacyl-tRNA synthesized by a natural aminoacyl-tRNA synthetase, an artificial aminoacyl-tRNA, in which a desired amino acid or hydroxy acid is linked (acylated) to the tRNA, may be used. Such aminoacyl-tRNA may be synthesized using an artificial ribozyme.

Such ribozymes include flexizyme (H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature Methods 3, 357-359 "The flexizyme system: a highly flexible tRNA aminoacylation tool for the synthesis of nonnatural peptides"; N. Niwa, Y. Yamagishi, H. Murakami, H. Suga (2009) Bioorganic & Medicinal Chemistry Letters 19, 3892-3894 "A flexizyme that selectively charges amino acids activated by a water-friendly leaving group"; and WO2007/066627, etc.). Flexizyme is also known by names such as the original flexizyme (Fx), and modified versions of it, such as dinitro benzyl flexizyme (dFx), enhanced flexizyme (eFx), and amino flexizyme (aFx).

By using tRNA linked with the desired amino acid or hydroxy acid produced by the flexizyme, a desired codon may be translated in association with the desired amino acid or hydroxy acid. A Special amino acid may be used as the desired amino acid. For example, the above-mentioned non-natural amino acids required for the cyclization may also be introduced into the hemagglutinin-binding peptide by this method.

Chemical synthesis of the macrocyclic peptides and analogs thereof of the present invention may be synthesized using various methods commonly used in the art, including stepwise solid-phase synthesis, semi-synthesis of a peptide fragment via conformationally supported religation, and chemical ligation. The synthesis of the peptides and the analogs thereof described herein is a chemical synthesis using various solid phase techniques as described in, for example, K. J. Jensen, P. T. Shelton, S. L. Pedersen, Peptide Synthesis and Applications, 2nd Edition, Springer, 2013, etc. The preferred strategy is based on the combination of an Fmoc group that temporarily protects the α-amino group and allows selective removal by a base, and a protecting group that temporarily protects a side chain functional group and is stable under deFmoc conditions. Such a general selection of peptide side chains is known for the above-mentioned Peptide Synthesis and Applications, 2nd edition, and G. B. Fields, R. L. Noble, Solid Phase Peptide Synthesis Utilizing 9-Fluorenylmethoxycarbonyl Amino Acids, Int. J. Peptide Protein Res. 35, 1990, 161-214, etc., however, preferred peptide side chain protecting groups include the Boc group and Mtt group for lysine and other amino groups, the tert-butyl group for the carboxyl group of glutamic acid and aspartic acid, and Trt group and Mmt group for the thiol group of cysteine.

The synthesis of the resin as a precursor for peptide synthesis in the present invention (or simply referred to as "resin") may be prepared by using, for example, commercially available PAL-PEG-resin and PAL-PEG-PS, etc., with reference to the reported examples such as Biopolymers 2011; 96 (6): 715-22. For example, an outline is shown in Scheme 1, wherein n denotes the length of the carbon number, R1 denotes hydrogen or an alkyl group with 1-4 carbons, R2 denotes various alkyl chains or alkyl chains having a substituent. The amino group of the resin 1 is sulfonylated with o-Ns-Cl in the presence of an appropriate base to prepare 2. The solid phase resin 4 may be obtained by reacting an amino primary alcohol 3 protected at the N-terminus with Fmoc such as Fmoc-glycinol, with a reagent used in combination with a Mitsunobu-type reaction such as triphenylphosphine, in the presence of diisopropyl azodicarboxylate, etc. Fmoc may be deprotected by a combination of an appropriate secondary amine in a solvent, such as DMF solution of piperidine, to yield 5, and various acyl groups may be introduced into the regenerated amine using a known peptide coupling method to yield 6. As for $R^2$, it may be introduced, for example, by reacting decanoic acid having a long chain alkyl group (composition formula $CH_3(CH_2)_8COOH$) in the presence of the condensing agents HATU and DIPEA. Finally, the resin 7, a precursor for the peptide synthesis, may be adjusted by treating the removal of the o-Ns group with a combination of an appropriate base and a thiol, such as DBU and DODT.

Scheme 1

[Formula 30]

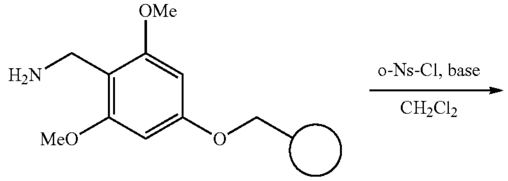

1
PAL-PEG resin
(PAL-PEG-PS)

-continued

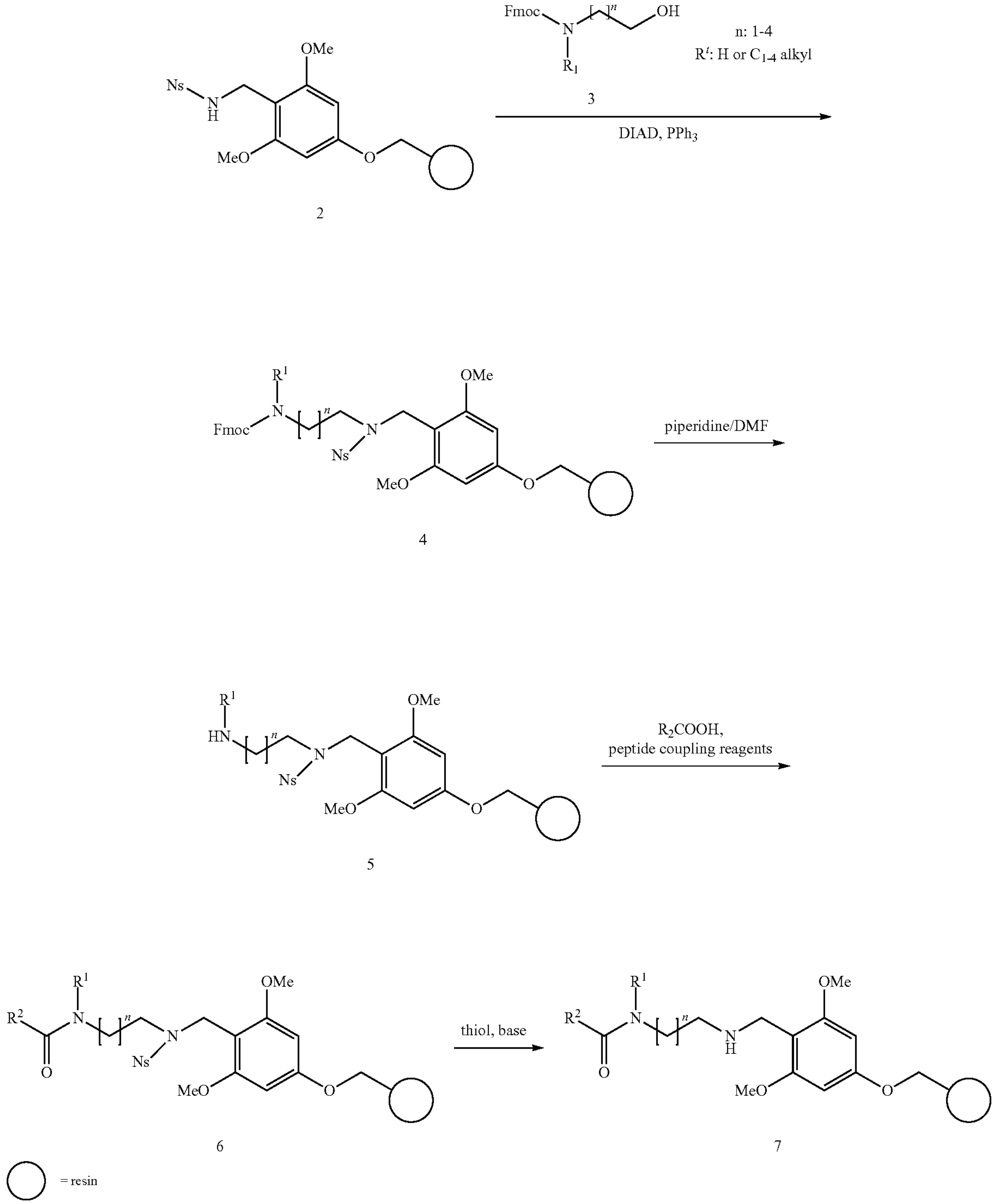

2, 3, 4, 5, 6, 7

In the peptide synthesis in the present invention, a commercially available resin may be used as another method. For example, an outline is shown in scheme-2. As another way to adjust one preferred precursor resin, commercially available Rink Amide MBHA resin (Sigma-Aldrich), Fmoc-Rink Amide NovaPEG resin (Merck Millipore), or Fmoc-NH-SAL-PEG resin (Watanabe Chemical Industries, LTD.) was used as a solid phase resin (8), after removal of Fmoc, Fmoc amino acid 9 having a primary or secondary amino group on the side chain having a protecting group that may be removed under mild acidic conditions, such as Fmoc-Lys (Mtt)-OH (m=3, $R^3$=H, S-configuration), may be condensed to obtain 10. The resulting solid-phase resin may be treated with a solution of $TFA/TIS/CH_2Cl_2$ in a volume ratio of 1:4:95 to selectively remove Mmt group to yield 11. Subsequently, after the introduction of $R^2COOH$ as described above, 12 is yielded, and with the removal of the Fmoc group, 13 may be yielded, which may be used for the synthesis of the target peptide.

Scheme 2
[Formula 31]
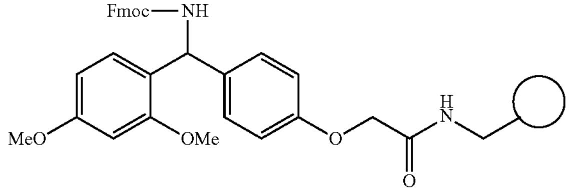
8
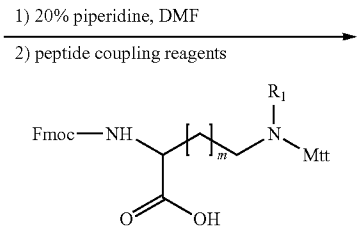
9
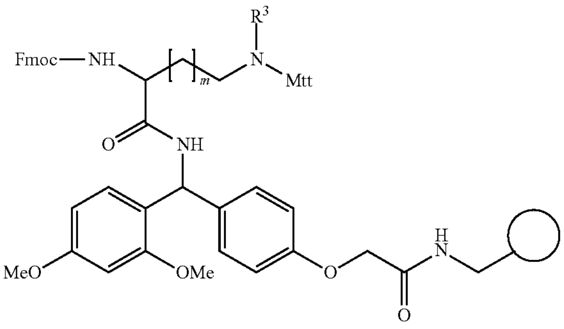
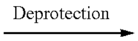
10
m: 0-4
$R^3$: H or $C_{1-4}$ alkyl
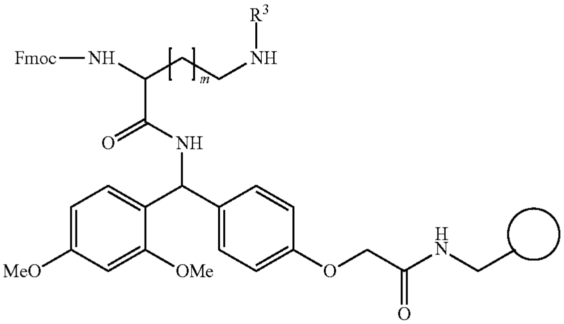
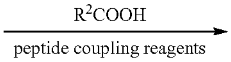
11
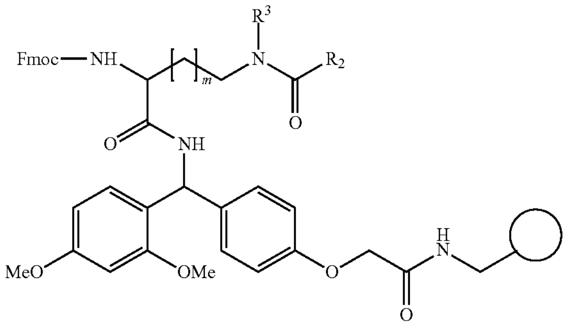
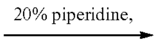
12

-continued

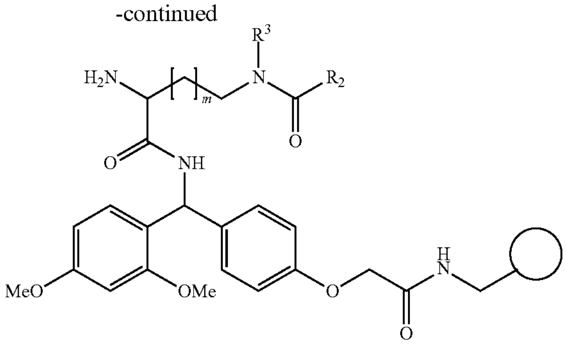

13

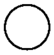

= resin

The peptides and analogs thereof described in the present invention may be synthesized in a stepwise method on the solid phase resin as described above. In the C-terminal amino acid used, and in all amino acids and peptides used in the synthesis, the α-amino protecting group must be selectively removed during the synthetic process. Preferably, using the above-mentioned solid phase resin, the C-terminal carboxyl group of a peptide whose N-terminus is appropriately protected using a protecting group such as Fmoc, or the C-terminal carboxyl group of an amino acid appropriately protected using a protecting group such as Fmoc, is made into an activated ester by an appropriate reagent and then added to an amino group on the solid phase resin to initiate the process. Subsequent elongation of the peptide chain may be achieved by sequentially repeating the removal of the N-terminal protecting group (e.g., Fmoc group), followed by condensation of the protected amino acid derivative, according to the amino acid sequence of the target peptide. These may liberate the target peptide in the final stage. For example, as a condition for liberation, it may be liberated with a TFA solution containing water/silyl hydride/thiol as a scavenger in TFA, which is described in Teixeira, W. E. Benckhuijsen, P. E. de Koning, A. R. P. M. Valentijn, J. W. Drijfhout, Protein Pept. Lett., 2002, 9, 379-385, etc. A typical example is TFA/Water/TIS/DODT (volume ratio 92.5:2.5:2.5:2.5).

The synthesis of the peptide analogs described herein may be carried out by using a single or multi-channel peptide synthesizer, such as CEM's Liberty Blue synthesizer or Biotage's Syro I synthesizer.

Activation of the carboxy group may be carried out using a condensing agent. The condensing agents include, for example, dicyclohexylcarbodiimide (DCC), diisopropylcarbodiimide (DIPCDI), 1-ethyl-3-(3-dimethylaminopropyl) carbodiimide (EDC or WSC), (1H-benzotriazol-1-yloxy)tris (dimethyl amino)phosphonium hexafluorophosphate (BOP), 1-[bis(dimethyl amino)methyl]-1H-benzotriazolium-3-oxide hexafluorophosphate (HBTU).

Another embodiment disclosed in this description relates to a medical drug. This medical drug includes the above-mentioned hemagglutinin-binding peptides, the pharmaceutically acceptable salts thereof, or solvates (for brevity, these will be referred to as simply hemagglutinin-binding peptides below). The medical drug preferably contains an effective amount of the above-mentioned hemagglutinin-binding peptide as an active ingredient.

When the hemagglutinin-binding peptide is used for a medical drug application, one or more of the amino acids in the peptide may be chemically modified, for example, with a hydrocarbon, a fatty acid, and polyethylene glycol (PEG), etc., for functionalizing and various modifications. In addition, these chemical modifications may also be carried out using a linker. These modifications may, for example, yield a peptide that are more chemically and metabolically stable. The linker is a substructure that allows a cyclic peptide that exhibits anti-virus activity (e.g., the basic structure shown in (II)) and chemical modification for functionalizing. Specific examples of the basic structure in the present invention are the 1,2-ethylenediamine structure represented in (I) and the lysin amide structure with $NH_2$ at the C-terminus represented in (II).

As shown in the examples below, the peptides of the present invention exhibit activity anti-virus by binding to a hemagglutinin on the surface of the virus. The type of virus is not particularly limited, as long as it exhibits anti-virus activity against viruses that infect humans, etc. via a hemagglutinin or a similar protein. The type of virus is, for example, an envelope virus, and more preferably, a virus having a class I fusion protein. Specific examples of the virus include seasonal influenza viruses (including human, avian, and swine influenza viruses or novel influenza viruses, also referred to as simply an influenza virus), highly pathogenic avian influenza viruses, swine epidemic diarrhea viruses, HIV-1, Ebola viruses, yellow fever viruses, and corona viruses. The target virus is preferably the influenza virus. In addition, the target influenza virus may be any of the A, B, and C types, but preferably the A type, and more preferably an influenza virus having the hemagglutinin belonging to Group I. Herein, anti-influenza virus activity is also referred to as anti-virus activity.

Compositions containing the peptides of the present invention are useful as a preventive drug for virus infection or a therapeutic drug for virus infectious diseases, preferably as a preventive or therapeutic agent for influenza, and similarly, the peptides of the present invention are useful in a method of preventing virus infections or treating virus infectious diseases, preferably in methods of preventing or treating influenza.

Herein, the term "influenza" means an acute infectious disease caused by the influenza virus. Infection with the influenza virus causes cold-like symptoms with high fever, muscle pain, etc., in humans. It may be accompanied by gastrointestinal symptoms such as abdominal pain, vomiting, and diarrhea, and complications include pneumonia and influenza encephalopathy.

Herein, the term "infection" is used to refer to either the process by which a virus invades a living body through the skin or mucous membrane, or the process by which a virus enters a cell through membrane fusion. In addition, herein, the term "virus infection" means the state in which a virus has invaded a living body, regardless of the presence or absence of symptoms. In addition, herein, the term "infectious disease" means various symptoms caused by a virus infection.

Herein, the term "therapy or prevention of influenza" is used in its broadest sense, and means, for example, relieving or preventing the worsening of one or more symptoms associated with influenza virus infection, suppressing the development of symptoms after infection, preventing (delaying or stopping) the infection of cells with the virus in vivo, preventing (delaying or stopping) the proliferation of the virus in vivo, a decrease in the number of viruses in vivo, etc. If at least one of these is effective, it is considered useful in the therapy or prevention of influenza. In addition, as shown in the examples below, the peptides of the present invention have neutralizing activity against the hemagglutinins, so it is understood that the same effect as influenza vaccine may be obtained.

Herein, the dosage form of the medical drug composition is not particularly limited and may be oral administration or parenteral administration. The parenteral administration includes, for example, injection administration such as intramuscular injection, intravenous injection, and subcutaneous injection, transdermal administration, and transmucosal administration (transnasal, transoral, transocular, transpulmonary, transvaginal, and transrectal) administration.

The above medical drug compositions may be modified in various ways in consideration of the property of the polypeptide to be easily metabolized and excreted. For example, polyethylene glycol (PEG) or a sugar chain may be added to the polypeptide to increase the residence time in the blood and reduce the antigenicity. In addition, bio-degradable polymer compounds such as poly (lactic-co-glycolic acid) (PLGA), porous hydroxyapatite, liposomes, surface-modified liposomes, emulsions prepared with unsaturated fatty acids, nanoparticles, nanospheres, etc. may be used as sustained release base agents, and the polypeptide may be encapsulated in them. If administered transdermally, a weak electric current may be applied to the skin surface to penetrate the stratum corneum (iontophoresis method).

The above medical drug compositions may be used as the active ingredients as they are, or may be formulated by adding pharmaceutically acceptable carriers, excipients, additives, etc. Examples of dosage forms include liquids (e.g., injections), dispersants, suspensions, tablets, rounds, powders, suppositories, sprays, fine granules, granules, capsules, syrups, lozenges, inhalants, ointments, eye drops, nasal drops, ear drops, and papules.

The formulation may be carried out by a conventional method, for example, using an excipient, a binder, a disintegrant, a lubricant, a dissolving agent, a dissolution aid, a colorant, a taste and odor correcting agent, a stabilizer, an emulsifier, an absorption enhancer, a surfactant, a pH adjuster, a preservative, an antioxidant, etc. as appropriate.

Examples of ingredients used in formulation include, but are not limited to, pharmaceutically acceptable organic solvents such as purified water, saline solution, phosphate buffer solution, dextrose, glycerol and ethanol, animal and vegetable oils, lactose, mannitol, glucose, sorbitol, crystal cellulose, hydroxypropyl cellulose, starch, cornstarch, silicic acid anhydride, magnesium aluminum silicate, collagen, polyvinyl alcohol, polyvinylpyrrolidone, carboxyvinyl polymer, sodium carboxymethyl cellulose, sodium polyacrylate, sodium alginate, water-soluble dextran, carboxymethyl starch, pectin, methyl cellulose, ethyl cellulose, xanthan gum, gum arabic, tragacanth, casein, agar, polyethylene glycol, diglycerin, glycerin, propylene glycol, vaseline, paraffin, octyl dodecyl myristate, isopropyl myristate, higher alcohol, stearyl alcohol, stearic acid, human serum albumin.

In consideration of the fact that the peptide is difficult to be absorbed through the mucosa, the above medical drug compositions may contain an absorption enhancer that improve absorption of poorly absorbable drugs. As such absorption enhancers, surfactants such as polyoxyethylene lauryl ethers, sodium lauryl sulfate, and saponins; bile salts such as glycocholic acid, deoxycholic acid, and taurocholic acid; chelating agents such as EDTA and salicylic acids; fatty acids such as caproic acid, capric acid, lauric acid, oleic acid, linoleic acid, and mixed micelles; enamine derivatives, N-acyl collagen peptides, N-acylamino acids, cyclodextrins, chitosan, nitric oxide donor, etc. may be used.

The rounds or tablets may also be coated with sugar coating, gastric soluble and enteric soluble substances.

Injectable formulations may contain distilled water for injection, physiological saline solution, propylene glycol, polyethylene glycol, vegetable oils, alcohols, etc. Furthermore, a wetting agent, an emulsifier, a dispersant, a stabilizer, a dissolving agent, a dissolving aid, a preservative may be added.

If the medical drug compositions of the present invention is administered to mammals (e.g., humans, mice, rats, guinea pigs, rabbits, dogs, horses, monkeys, pigs, etc.), especially humans, the dosage varies depending on the symptoms, age, gender, weight, sensitivity difference of the patient, administration method, administration interval, type of active ingredient, and type of formulation, and is not particularly limited, but for example, 30 μg-100 g, 100 μg-500 mg, or 100 μg-100 mg may be administered once or several times. In case of the injection administration, depending on the weight of patient, 1 μg/kg-3000 μg/kg, 3 μg/kg-1000 μg/kg may be administered once or several times.

The methods of preventing or treating influenza using the peptides of the present invention may be carried out with reference to the description for the above medical drug compositions.

Another embodiment disclosed in this description relates to a virus detection agent, in particularly an influenza virus detection agent. This virus detection agent contains the above-mentioned hemagglutinin-binding peptide, the salt thereof, or the solvate thereof.

(Virus Detection Agents and Detection Kits)

The present invention also encompasses virus detection agents, in particularly influenza virus detection agents, containing the peptides of the present invention. The peptides of the present invention specifically bind to a hemagglutinin on the surface of a virus. Therefore, for example, the peptides of the present invention may be used in place of anti-influenza antibodies in immunoassays such as ELISA method to detect influenza viruses in a sample.

The peptides of the present invention may be detectably labeled if used as a detection agent. The peptides may be labeled with known labeling substances, for example, the peptides labeled with enzymes such as peroxidase and alkaline phosphatase, radioactive substances such as 125I, 131I, 35S and 3H, fluorescent substances such as fluorescein isothiocyanate, rhodamine, dansyl chloride, phycoerythrin, tetramethyl rhodamine isothiocyanate, and near-infrared fluorescent substances, and luminescent substances such as luciferase, luciferin, and equilin are used. In addition, the peptides labeled with nanoparticles such as gold colloids, quantum dots may also be detected.

In addition, in immunoassays, the peptides of the present invention may be labeled with biotin and bound to avidin or streptavidin labeled with enzymes, etc. for detection.

Among immunoassays, ELISA method using enzymatic labeling is preferable because antigens may be measured easily and quickly. For example, an antibody that specifically recognize a moiety of an influenza virus other than the hemagglutinin are fixed to a solid phase carrier, and a sample is added and reacted, followed by the labeled peptides of the present invention is added and reacted. The influenza virus may be detected by washing it and then reacting it with an enzyme substrate, developing a color, and measuring the absorbance. After reacting the antibody immobilized on the solid phase carrier and the sample, unlabeled peptides of the present invention are added, and an antibody to the peptides of the present invention may be enzymatically labeled and further added. In addition, the peptides of the present invention are immobilized to a solid phase carrier as a capture substance, and the labeled antibodies that recognize influenza viruses may be used as a detection substance, or the peptides of the present invention may be used for either capture or detection.

In the enzyme substrate, if the enzyme is peroxidase, 3,3'-diaminobenzidine (DAB), 3,3',5,5'-tetramethylbenzidine (TMB), o-phenylenediamine (OPD), etc. may be used, and if the enzyme is alkaline phosphatase, p-nitrophenyl phosphate (NPP), etc. may be used.

Herein, the "solid phase carrier" is not particularly limited as long as it is a carrier on which the peptides may be immobilized, and includes microtiter plates made of glass, metal, resin, etc., substrates, beads, nitrocellulose membranes, nylon membranes, PVDF membranes, and the target substances may be immobilized on these solid phase carriers according to known methods.

The inspection kit according to the present invention includes reagents and instruments necessary for the above detection (including, but not limited to, peptides of the present invention, antibodies, solid phase carriers, buffer solutions, enzyme reaction termination solutions, microplate readers).

Another embodiment disclosed in this description may also be considered for use as an influenza virus detection kit containing the above-mentioned influenza virus detection agent, or as a tool to elucidate hemagglutinin-mediated influenza virus infection, and various cellular functions and life phenomena associated with it.

This description also provides the use of hemagglutinin-binding peptide to produce a medical drug for the prevention or therapy of influenza. In this case, the hemagglutinin-binding peptide may be any of the above-mentioned ones.

The present description also provides a method of preventing or treating influenza including the step of administering an effective amount of the hemagglutinin-binding peptide, the pharmaceutically acceptable salt thereof, or the solvate thereof as an active ingredient to a subject that is a human, a non-human mammal, or an avian. As the hemagglutinin-binding peptide, the above-mentioned peptides may be used as appropriate. Examples of the non-human mammal are non-human primates, pigs, cattle, dogs, cats, horses, sheep, rats and mice.

The abbreviations used herein, particularly in the following representative examples, are well known to those skilled in the art. Some of the abbreviations used are as follows: Fmoc as 9-fluorenylmethyloxycarbonyl; HOAt as 1-hydroxybenzotriazole; HATU as 0-(7-azabenzotriazol-1-yl)-N,N,N',N'-tetramethyluronium hexafluorophosphate; MeCN as acetonitrile; DBU as 1,8-diazabicyclo "5.4.0"-7-undecene; DIPEA as N,N-diisopropylethylamine; DODT as 3,6-dioxa-1,8-octane-dithiol; DMSO as sulfoxide; dimethyl DMF as N,N-Dimethylformamide; mL as milliliter (unit); M as molar (unit); Mtt as monomethyl trityl; Mmt as monomethoxy trityl; o-Ns as 2-nitrobenzenesulfonyl; v/V as volume/volume; TFA as trifluoroacetic acid; TIS as triisopropylsilane; Trt as trityl.

EXAMPLES AND GENERAL METHODS

All the raw materials, building blocks, reagents, acids, bases, solid phase resins, and solvents used in the chemical synthesis of the present invention were either commercially available or may be synthesized by those skilled in the art using organic chemical methods. Unless otherwise specified, amino acids containing protecting groups were used as they are commercially available products.

In the present invention, a structure determination of the chemically synthesized peptides was confirmed by ESI-MS (+) in the mass spectrum analysis method with molecular weights calculated considering amino acids used according to the target sequence and building blocks used as needed. The term "ESI-MS (+)" means an electrospray ionization mass spectrum analysis method carried out in the positive ion mode. The detected masses were reported in "m/z" units. Compounds with molecular weights greater than approximately 1000 were detected frequently as divalent or trivalent ions.

In the present invention, the purity of the chemically synthesized peptides was determined by one of the following analytical methods.

(Analysis Conditions)

Analysis Condition A

Column: CORTECS (registered trademark) UPLC (registered trademark) C18 column (Nihon Waters), 90 Å, 1.6 μm, 2.1×100 mm Mobile phase: MeCN/0.025% TFA in $H_2$ Temperature: 40° C.

Gradient: 5-95% MeCN/0.025% TFA in H2 in 5.56 min; linear gradient

Flow rate: 0.4 mL/min

Detection method: UV 220 nm

Analysis condition B

Column: Kinetex EVO C18 2.6 μm, 2.1 ID×150 mm, 100 Å (Phenomenex)

Column temperature: 60° C.

Mobile phase A: 0.025% TFA in H2

Mobile phase B: 0.025% TFA in $CH_3CN$

Gradient: as described in each example

Flow velocity: 0.25 mL/min

Detection: PDA (225 nm)

Elongation of the peptide chain in the solid phase resin described in the present invention was carried out using the resin described in each example as a starting material and using peptide coupling reaction conditions and Fmoc removal reaction conditions normally used. The reaction was carried out using CEM Liberty Blue, an automated peptide synthesizer, according to the manufacturer's manual. Common amino acids used are listed below, and side chain protecting groups are shown in parentheses. Fmoc-Trp (Boc)-OH; Fmoc-Thr (tBu)-OH; Fmoc-N-Me-Gly-OH; Fmoc-Asp (OtBu)-OH; Fmoc-N-Me-Phe-OH; Fmoc-Ala-OH; Fmoc-N-Me-Ala-OH; Fmoc-His (Trt)-OH; Fmoc-Tyr (tBu)-OH; Fmoc-Val-OH; Fmoc-HydPro (tBu)-OH; Fmoc-Cys (Trt)-OH; Fmoc-Lys (Mtt)-OH; Fmoc-Ser (tBu)-OH; Fmoc-N-Me-Ser (tBu)-OH.

The introduction of the chloroacetyl group was carried out by removing the Fmoc group of the α-amino group from the solid phase resin holding the Fmoc-protected peptide obtained in the previous step by the method described above, followed by adding chloroacetic acid (about 3 equiv.), about 3 equiv. of N,N'-diisopropylcarbodiimide in DMF solution (0.5 M), and about 3 equiv. of HOAt in DMF solution (0.5 M) and shaking at room temperature for 40 minutes.

For deprotection of the side chain and cutting out from the solid phase resin, the resin obtained after the chloroacetyl group introduction step was first washed five times with DMF and methylene chloride, respectively, and dried under reduced pressure. Subsequently, reactant cocktail—A (a mixture of TFA/$H_2$/TIS/DODT in a volume ratio of 92.5: 2.5:2.5:2.5) was added to the reaction vessel containing the solid phase resin and shaken at room temperature for 150 minutes. The reaction solution was collected from the frit by filtration. The solid phase resin remaining in the reaction vessel was shaken again with the cut-out cocktail, and the solution component was collected from the frit and mixed with the above-mentioned filtrate. If this filtrate was added to an excess of diethyl ether cooled to 0° C., a cloudy precipitate formed. This mixture was centrifuged (9000 rpm, 3 min) and the solution was decantated. The resulting solid was washed again with a small amount of diethyl ether cooled to 0° C., and then the resulting solid was used for the next cyclization reaction.

In the present invention, the cyclization reaction of the peptides was carried out by dissolving the peptides in DMSO to a final concentration of 5 mM, based on the number of moles of the solid phase resin, and then adding 6 equiv. of triethylamine and stirring at room temperature for about 16 hours. The resulting reaction solution was acidified with acetic acid and concentrated under reduced pressure using Biotage (registered trademark) V-10 (Biotage Japan).

As the method for purifying the resulting crude purified peptides, reversed-phase preparative HPLC on Waters Auto Purification System—SQD2 single quadruple mass spectrometer was used, elution was carried out while monitoring m/z ion derived from the target object. It was confirmed that the mass spectrum obtained in the scan mode of ESI-positive and the mass spectrum containing the multivalent ions calculated from the molecular formula of the target object match within the error range of the mass spectrometer used. The purification conditions, including the columns used, are shown in each example.

Example 1

Synthesis of HA119

[Formula 32]

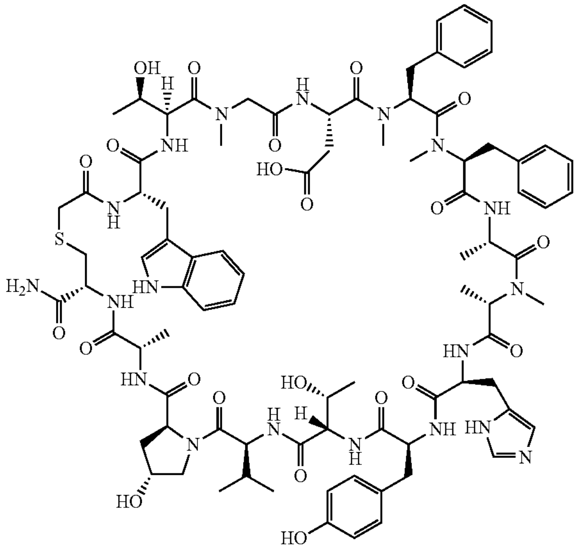

Fmoc-NH-SAL-PEG resin (Watanabe Chemical, 0.15 mmol/g, 0.43 g) was used to synthesize the target peptide, starting with the removal of Fmoc according to the above-mentioned general method. The chloroacetyl group was subsequently introduced according to the general method.

The resulting crude product was purified using the following conditions (column: Waters Xbridge (registered trademark) C18 5 μm OBD (registered trademark) 19×150 mm (Nihon Waters); mobile phase: A=0.1% TFA in $H_2O$, B=0.1% TFA in MeCN; temperature: 40° C.; gradient (% B): 5-29% over 3 min, then 29-34% over 8 min; flow rate: 17 mL/min).

The purity of the target object was calculated from the area ratio of the LC/MS (UV wavelength 225 nm) chromatogram under the analytical condition B, and was 99.4%.

Analysis condition A: retention time=3.57 min, ESI-MS (+) observed value m/z=899.8, theoretical value 899.5 ((M/2)+H)

Analysis condition B: retention time=16.5 min; gradient (% B conc): 25-65% over 20 min, then 65-95% over 1 min, then 95% over 5 min.

Example 2

Synthesis of HA146

[Formula 33]

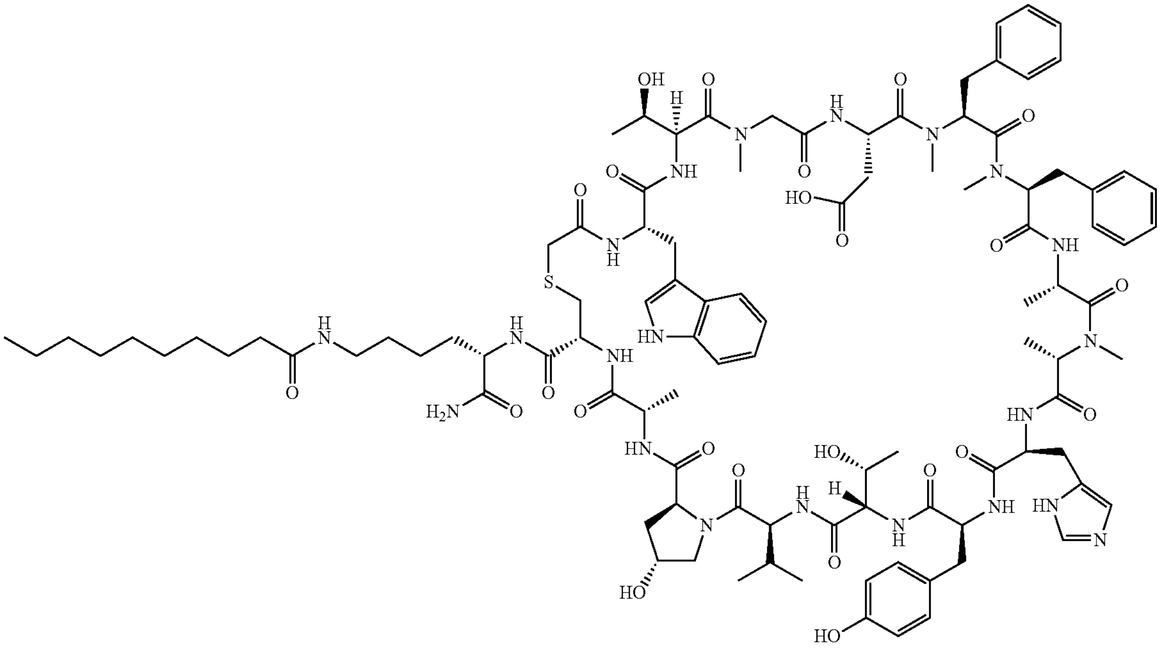

Fmoc-NH-SAL-PEG resin (Watanabe Chemical, 0.37 mmol/g, 1.35 g) was placed in a reaction vessel with a frit, shaken with dichloromethane and allowed to expand. Fmoc-Lys (Mtt)-OH was introduced into the resulting solid phase resin by peptide coupling after removal of Fmoc according to the above-mentioned general method. The resulting solid phase resin was swollen with dichloromethane, reactant cocktail-B (TFA/TIS/$CH_2Cl_2$ by volume ratio 1:4:95) was added, the solid phase resin was shaken at room temperature for 30 min, and then the reaction solution was drained from the frit. After repeating this operation 12 times, the color of the filtrate became colorless and transparent. This point was considered the completion of the reaction. To the resulting solid phase resin, a DMF solution of decanoic acid (0.21 M, 12 mL), a DMF solution of HATU (0.5 M, 5 mL), and a DMF solution of DIPEA (1 M, 5 mL) were added, and the mixture was shaken at 40° C. for 40 min. After the reaction solution was drained from the frit, the resulting solid phase resin was washed with DMF, followed by dichloromethane.

Fmoc was removed from the solid phase resin obtained by the above operation, and Fmoc-amino acids were sequentially introduced utilizing the automated synthesizer in the above-mentioned general method. The amino acid and reagent used in the reaction were calculated in equal amounts, assuming that the solid phase resin was 0.5 mmol. The peptide coupling was carried out by the automated synthesizer, subsequently, chloroacetyl group was introduced according to the above-mentioned general approach.

Subsequently, the resulting solid phase resin was used to deprotect the side chain, cut out from the solid phase resin, and carry out a cyclization reaction according to the above-mentioned general method.

The resulting crude product was purified using the following conditions (column; Waters Xbridge (registered trademark) C18 5 μm OBD (registered trademark) 50×250 mm (Nihon Waters); mobile phase: A=0.1% TFA in $H_2O$, B=0.1% TFA in MeCN; temperature: 40° C.; gradient (% B): 16-41% over 3 min, then 47-52% over 7 min, then 47-80% over 1.5 min; flow rate: 120 mL/min).

The purity of the target object was calculated from the area ratio of the LC/MS (UV wavelength 225 nm) chromatogram under the analytical condition B, and was 99.3%.

Analysis condition A: retention time=4.50 min, ESI-MS (+) observed value m/z=1040.4, theoretical value 1040.2 ((M/2)+H)

Analysis condition B: retention time=18.8 min; gradient (% B conc): 25-65% over 20 min, then 65-95% over 1 min, then 95% over 5 min.

Example 3

Synthesis of HA145

[Formula 34]

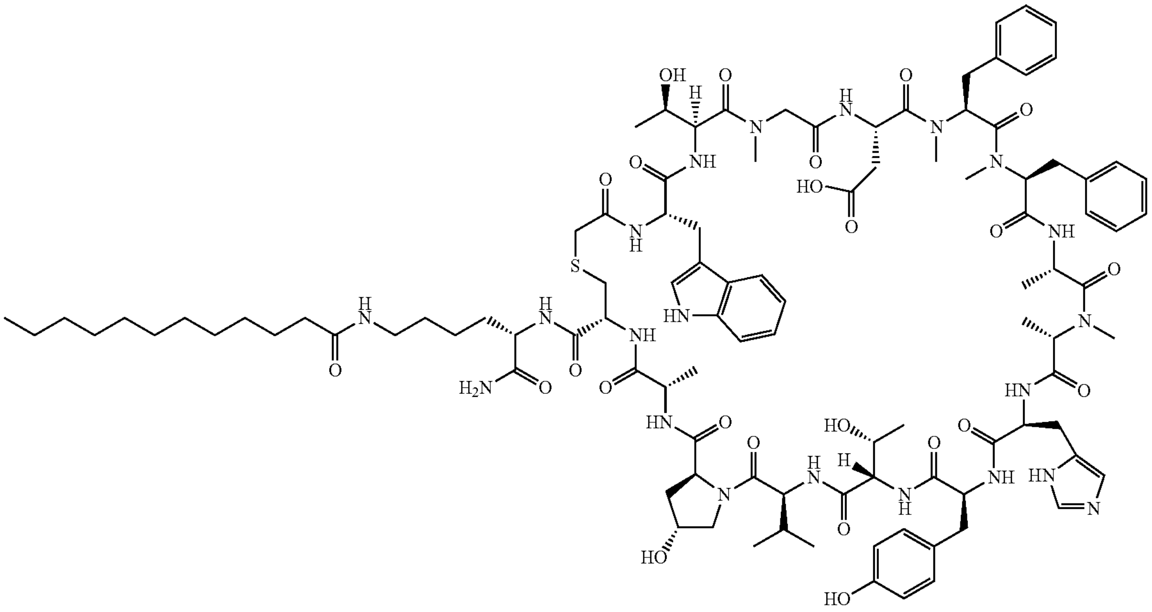

HA145 was synthesized according to the synthesis method shown in Example 1, using lauric acid instead of decanoic acid.

The resulting crude product was purified using the following conditions (column: Waters Xbridge (registered trademark) C18 5 m OBD (registered trademark) 50×250 mm (Nihon Waters); mobile phase: A=0.1% TFA in $H_2O$, B=0.1% TFA in MeCN; temperature: 40° C.; gradient (% B): 21-46% over 3 min, then 46-51% over 7 min, then 51-80% over 1.5 min; flow rate: 120 mL/min).

The purity of the target object was calculated from the area ratio of the LC/MS (UV wavelength 225 nm) chromatogram under the analytical condition B, and was 99.3%.

Analysis condition A: retention time=4.42 min, ESI-MS (+) observed value m/z=1055.1, theoretical value 1054.3 ((M/2)+H)

Analysis condition B: retention time=18.8 min, gradient (% B conc): 25-65% over 20 min, then 65-95% over 1 min, then 95% over 5 min.

Example 4

Synthesis of HA152

[Formula 35]

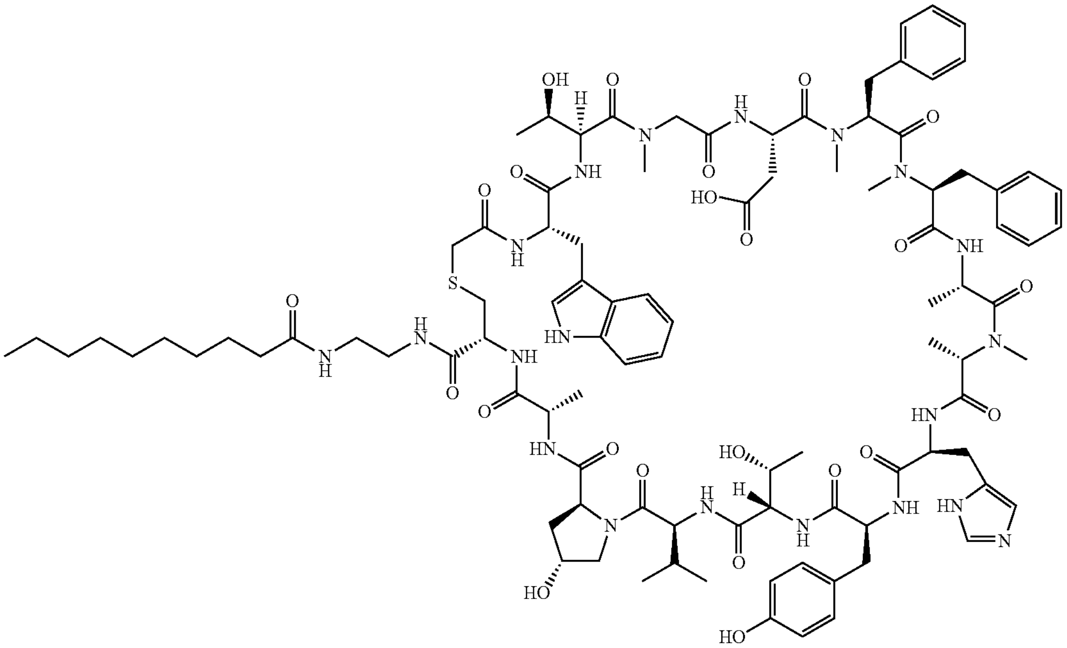

PAL-PEG resin (Watanabe Chemical, 0.22 mmol/g, 1.16 g) was placed in a reaction vessel with a frit, shaken with dichloromethane and allowed to expand. After draining from the dichloromethane frit, a dichloromethane solution (5 mL) of 2-nitrobenzenesulfonyl chloride (4 equiv.) and a dichloromethane solution (4 mL) of DIPEA (4 equiv.) were added and the mixture was stirred at room temperature for 30 min. After the reaction solution was drained from the frit, the solid phase resin was washed with dichloromethane. To the resulting solid phase resin, a THF solution (6 mL) of Fmoc-glycinol (10 equiv.), a dichloromethane solution (5 mL) of triphenylphosphine (12 equiv.), and a dichloromethane solution (5 mL) of diisopropyl azodicarboxylate (10 equiv.) were added and the mixture was shaken at room temperature. The progress of the reaction was confirmed by LCMS after a small amount of the solid phase resin was taken out and treated with a cut-out cocktail. After the reaction solution was drained from the frit, the solid phase resin was washed with dichloromethane. To the resulting solid phase resin, a DMF solution (12 mL) of piperidine (20%) was added and the mixture was shaken at room temperature for 30 min. The reaction solution was drained from the slit, and the DMF solution (12 mL) of piperidine (20%) was added again and the mixture was shaken at room temperature for 30 min. After the reaction solution was drained from the slit, the resulting solid phase resin was washed with DMF, followed by dichloromethane. To the resulting solid phase resin, a DMF solution of decanoic acid (0.21 M, 5 mL), a DMF solution of HATU (0.5 M, 2 mL), and a DMF solution of DIPEA (1 M, 2 mL) were added, and the mixture was shaken at 40° C. for 1 hour. After the reaction solution was drained from the frit, the resulting solid phase resin was washed with DMF, followed by dichloromethane. The resulting solid phase resin was immersed in 10 mL of DMF, and DODT (0.4 mL, 10 equiv.) and DBU (0.37 mL, 10 equiv.) were added, and the mixture was stirred at room temperature. The progress of the reaction and the disappearance of the raw material were confirmed by LCMS after treating a small amount of the solid phase resin.

Fmoc-amino acids were sequentially introduced into the solid phase resin obtained by the above operation, utilizing the automated synthesizer in the above-mentioned general method. The amino acid and reagent used in the reaction were calculated in equal amounts, assuming that the solid phase resin was 0.25 mmol. The peptide coupling was carried out by the automated synthesizer, subsequently, chloroacetyl group was introduced according to the above-mentioned general approach.

The resulting solid phase resin was used to deprotect the side chain, cut out from the solid phase resin, and carry out a cyclization reaction according to the above-mentioned general method.

The resulting crude product was purified using the following conditions (column: Waters Xbridge (registered trademark) C18 5 μm OBD (registered trademark) 50×250 mm (Nihon Waters); mobile phase: A=0.1% TFA in $H_2O$, B=0.1% TFA in MeCN; temperature: 40° C.; gradient (% B): 17-42% over 3 min, then 42-47% over 7 min, then 47-80% over 1.5 min; flow rate: 120 mL/min).

The purity of the target object was calculated from the area ratio of the LC/MS (UV wavelength 225 nm) chromatogram under the analytical condition B, and was 98.4%.

Analysis condition A: retention time=4.18 min, ESI-MS (+) observed value m/z=998.6, theoretical value 998.2 ((M/2)+H).

Analysis condition B: retention time=16.48 min, gradient (% B conc): 25-65% over 20 min, then 65-95% over 1 min, then 95% over 5 min.

Example 5

Synthesis of HA151

[Formula 36]

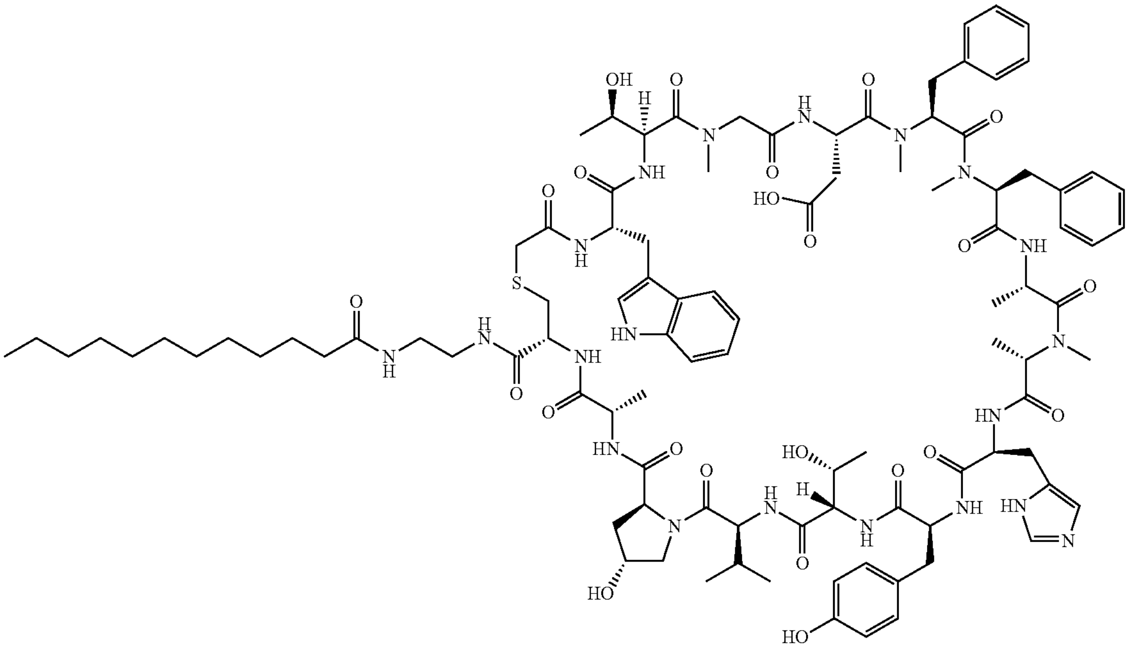

HA151 was synthesized according to the synthesis method shown in Example 4, using lauric acid instead of decanoic acid.

The resulting crude product was purified using the following conditions (column; Waters Xbridge® C18 5 μm OBD® 50x250 mm; mobile phase: A=0.1% TFA in $H_2O$, B=0.1% TFA in MeCN; temperature: 40° C.; gradient (% B): 22-47% over 3 min, then 47-52% over 7 min, then 52-80% over 1.5 min; flow rate: 120 mL/min).

The purity of the target object was calculated from the area ratio of the LC/MS (UV wavelength 225 nm) chromatogram under the analytical condition B, and was 97.7%.

Analysis condition A: retention time=4.49 min, ESI-MS (+) observed value m/z=1012.4, theoretical value 1012.2 ((M/2)+H)

Analysis condition B: retention time=12.5 min, gradient (% B conc): 40-80% over 20 min, then 80-95% over 1 min, then 95% over 5 min.

Example 6

[Evaluation of the Anti-Virus Activity of the Peptides Against Influenza Viruses.]

In order to confirm the in vitro anti-virus activity of the peptides against influenza viruses, the test was carried out by the method shown below. The specific test method is shown below.

1) MDCK cells were seeded at $3\times10^4$ cells/well and cultured at 37° C., 5% $CO_2$, in the presence of MEM-10% FBS for 24 hours.
2) after incubation, 100 μL of serum-free MEM was added to the well and the cell monolayer was washed.
3) the compounds to be tested were dissolved by an infection maintenance medium (serum-free MEM containing vitamins) and adjusted to each measured concentration.
4) a test compound dissolved in the serum-free MEM that is the infection maintenance medium were added to each well.
5) Influenza viruses A/Nagasaki/HA-58/2009 (H1N1), A/Puerto Rico/8/34 (H1N1), or A/Duck/Pennsylvania/84 (H5N2) was diluted with the infection maintenance medium containing trypsin to prepare 1,000 $TCID_{50}$/mL.
6) the diluted virus solution was added at 100 μL/well and the titer per well was adjusted to 100 $TCID_{50}$.
7) the viruses were incubated at 37° C., 5% CO2 conditions for 72 hours.
8) after completion of incubation, the culture medium was removed from each well.
9) a 70% ethanol aqueous solution was added at 200 ul/well and allowed to stand still at room temperature for 5 minutes.
10) after removing the ethanol aqueous solution, a 0.5% crystal violet aqueous solution was added at 200 μL/well and allowed to stand still at room temperature for 5 minutes.
11) it was rinsed with water and dried under room temperature.
12) TECAN infinite 200 (TECAN) was used to measure the absorbance of each well at the measurement wavelength of λ=560 nm.
13) at each concentration, the relative value (CV relative value, %) was calculated when the mock group (drug-free and virus-free group) was set at 100%.
14) GraphPad Prism 5.0 (GraphPad Software) was used to determine the EC50 value of each specimen.

In order to confirm the in vivo anti-virus activity of the peptides against influenza viruses, the test was carried out by the method shown below. The specific test method is shown below.

1) five BALB/cA Jcl [SPF] mice per group were adjusted as infection model mice.

2) the virus solution stored at −80° C. was gently melted on ice, centrifuged for a few seconds, and then dispensed into a tube containing PBS.
3) the anesthetized mice were nasally inoculated with influenza virus A/Puerto Rico/8/34 (H1N1) at 267 pfu per mouse, and the above-mentioned inoculation time point was set as "day 0".
4) HA152 was dissolved in a 10% hydroxypropyl-β-cyclodextrin solution that is a dissolving solvent.
5) Peramivir was dissolved in the PBS solution.
6) Peramivir and HA152 were administered intravenously in the tail at a dose of 30 μmol/kg and 15 μmol/kg, respectively. As a vehicle control, the 10% hydroxy-propyl-β-cyclodextrin solution was administered intravenously in the tail as well.
7) after influenza virus infection and compound administration, the condition was observed once a day, including life or death.
8) the survival rate was calculated by converting the survival rate for 14 days with the day of infection as day 0.

3. Result

Results of HA152 activity evaluation using influenza viruses A/Nagasaki/HA-58/2009 (H1N1), A/Puerto Rico/8/34 (H1N1), and A/Duck/Pennsylvania/84 (H5N2)

The results of in vitro evaluation of anti-virus activities of iHA100 and HA152 against influenza viruses A/Nagasaki/HA-58/2009 (H1N1), A/Puerto Rico/8/34 (H1N1), and A/Duck/Pennsylvania/84 (H5N2) are shown in FIG. 1. iHA100 inhibited virus-induced cell death in the high concentration range of 1 μM or more in the final concentration, but did not show remarkable inhibition of cell death in the low concentration range of nM range. On the other hand, HA152 was found to show remarkable inhibition of cell death even in low concentration range of μM or less, and have remarkable anti-virus activity against both human and avian test influenza viruses, even in low concentration range. This confirmed that HA152 showed extremely high anti-influenza virus activity compared to iHA100.

Next, using influenza virus A/Duck/Pennsylvania/84 (H5N2), the in vitro anti-virus activity of the compounds containing iHA100 and HA152 was calculated as EC50. As shown in FIG. 2, the compound containing HA152 showed at least 10 times higher anti-virus activity than iHA100. Therefore, it was shown that HA152 and each compound shown in FIG. 2 retains remarkable higher anti-virus activity compared to iHA100.

Figure 3:
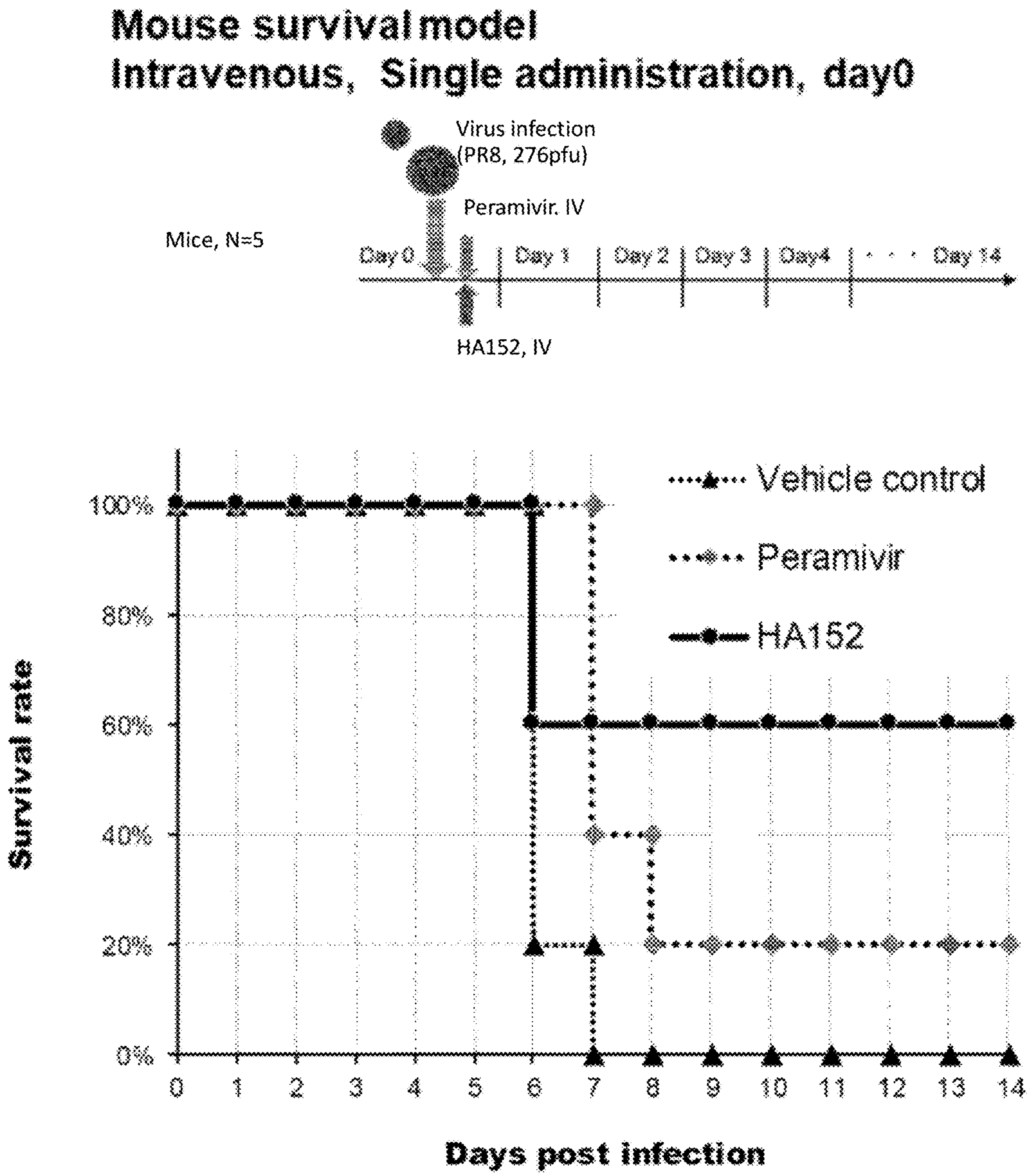
FIG. 3 is a graph showing analysis result of in vivo anti-influenza virus activity of HA152 using the influenza virus A/Puerto Rico/8/34 (H1N1) infection model.

Results of HA152 Activity Evaluation Using the Influenza Virus A/Puerto Rico/8/34 (H1N1) in a Mouse Infection Model The results of in vivo anti-virus activity evaluation of peramivir and HA152 using the influenza virus A/Puerto Rico/8/34 (H1N1) are shown in FIG. 3.

An analysis of the survival rate of mice infected with the influenza virus over 14 days showed that the survival rate for the group that did not receive the drug was 0%. On the other hand, the survival rate of the group receiving a single dose of 30 μmol/kg of peramivir was 20%, whereas the survival rate of the group receiving 15 μmol/kg of HA152 was 60%. This indicates that HA152 exhibited remarkable anti-virus activity not only in vitro, but also in vivo. Its anti-virus activity was comparable or superior to peramivir that is an approved pharmaceutical product that targets neuraminidase.

INDUSTRIAL APPLICABILITY

This invention may be utilized in the medical drug and medical device industries.

What is claimed is:

1. A hemagglutinin-binding peptide, a pharmaceutically acceptable salt thereof, or a solvate thereof, wherein the hemagglutinin-binding peptide is:

(1) a polypeptide consisting of an amino acid sequence represented by SEQ ID NO: 1 or 2:

```
                                         (SEQ ID NO: 1)
Trp-Thr-MeGly-Asp-MePhe-MePhe-Ala-MeAla-His-Tyr-

Thr-Val-hydPro-Ala-Cys,
and

                                         (SEQ ID NO: 2)
Trp-Thr-MeGly-Asp-MePhe-MePhe-Ala-MeAla-His-Tyr-

Thr-Val-hydPro-Ala-Cys-Lys;
```

(2) a polypeptide consisting of an amino acid sequence in which, in the SEQ ID NO: 1 or 2, the N-terminal Trp is chloroacetyl-Trp;

(3) a polypeptide consisting of an amino acid sequence in which, in the SEQ ID NO: 1, the N-terminal Trp is chloroacetyl-Trp and the C-terminal Cys has been modified as represented by Formula (I) via an amide bond;

(4) a polypeptide consisting of a sequence in which, in the SEQ ID NO: 2, the N-terminal Trp is chloroacetyl-Trp and the C-terminal Lys has been substituted with a modified lysine derivative represented by Formula (II);

(5) a polypeptide consisting of an amino acid sequence in which, in the SEQ ID NO: 1, the C-terminal Cys has been modified as represented by Formula (I) via an amide bond;

(6) a polypeptide consisting of a sequence comprising a lysine derivative represented by Formula (II) in which, in the SEQ ID NO: 2, a side chain of Lys has been modified with an acyl group; or (7) a peptide having an amino acid sequence in which, in the amino acid sequence in any of (1) to (6) above, one or two amino acids have been added or substituted to the C-terminal Cys in the SEQ ID NO: 1 or to the C-terminal Lys in the SEQ ID NO: 2 (however a sequence in which, in the SEQ ID NO: 1, the C-terminal Cys has been deleted, and a sequence in which, in the SEQ ID NO: 2, the C-terminal Lys has been deleted, are excluded)

Formula (I)

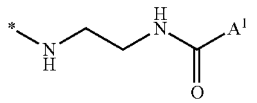

(In Formula (I), * denotes a linking moiety to a carbonyl group of the C-terminal Cys, and $A^1$ denotes a $C_8$-$C_{12}$ alkyl group)

Formula (II)

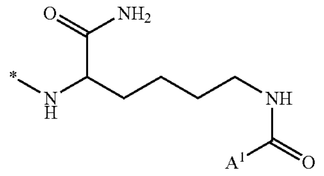

(In Formula (II), * denotes a linking moiety to a carbonyl group of the C-terminal Cys, and $A^1$ denotes a $C_8$-$C_{12}$ alkyl group).

2. The hemagglutinin-binding peptide, the pharmaceutically acceptable salt thereof, or the solvate thereof according to claim 1, wherein the hemagglutinin-binding peptide is:

(1) the polypeptide consisting of the amino acid sequence represented by the SEQ ID NO: 1 or 2:

```
                                         (SEQ ID NO: 1)
Trp-Thr-MeGly-Asp-MePhe-MePhe-Ala-MeAla-His-Tyr-

Thr-Val-hydPro-Ala-Cys,
and

                                         (SEQ ID NO: 2)
Trp-Thr-MeGly-Asp-MePhe-MePhe-Ala-MeAla-His-Tyr-

Thr-Val-hydPro-Ala-Cys-Lys;
```

(5) the polypeptide consisting of the amino acid sequence in which, in the SEQ ID NO: 1, the C-terminal Cys has been modified as represented by Formula (I) via an amide bond;

(6) a polypeptide consisting of a sequence in which, in the SEQ ID NO: 2, the C-terminal Lys has been substituted with a modified lysine derivative represented by Formula (II); or (7) a peptide having an amino acid sequence in which, in the amino acid sequence in any of (1), (5) and (6) above, one or two amino acids have been added or substituted to the C-terminal Cys in the SEQ ID NO: 1 or to the C-terminal Lys in the SEQ ID NO: 2 (however the sequence in which, in the SEQ ID NO: 1, the C-terminal Cys has been deleted, and the sequence in which, in the SEQ ID NO: 2, the C-terminal Lys has been deleted, are excluded).

3. The hemagglutinin-binding peptide, the pharmaceutically acceptable salt thereof, or the solvate thereof according to claim 1, wherein the hemagglutinin-binding peptide is cyclic.

4. The hemagglutinin-binding peptide, the pharmaceutically acceptable salt thereof, or the solvate thereof according to claim 3, wherein the hemagglutinin-binding peptide is represented by the following Formula (III) or (IV)

[Formula (III)]

(III)

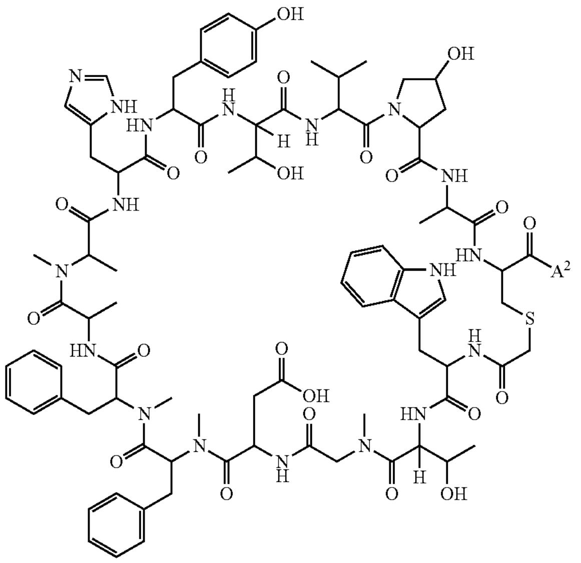

(In Formula (III), Formula $A^2$ denotes a group represented by —$NH_2$ or a group represented by Formula (I))

[Formula (IV)]

(IV)

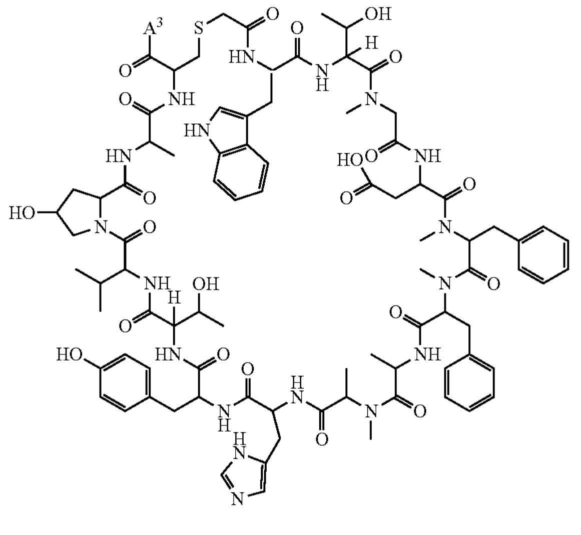

(In Formula (IV), Formula $A^3$ denotes a group represented by —$NH_2$ or Formula (II)).

5. The hemagglutinin-binding peptide, the pharmaceutically acceptable salt thereof, or the solvate thereof according to claim 3, wherein the hemagglutinin-binding peptide is represented by the following Formula (V) or (VI)

[Formula (V)]

(V)

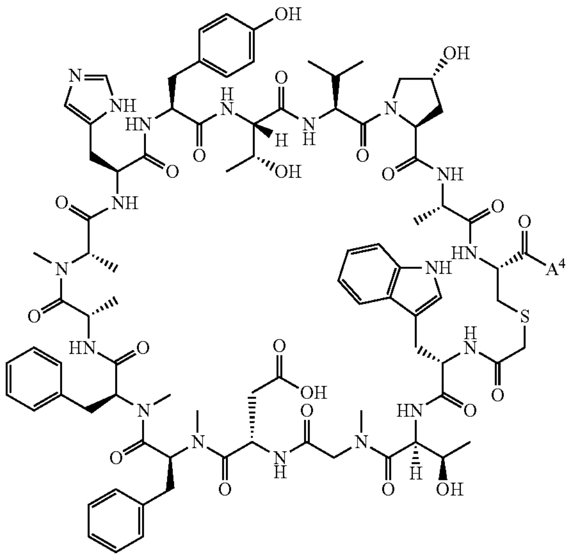

(In Formula (V), Formula $A^4$ denotes a group represented by —$NH_2$ or a group represented by —$NH_2$ or a group represented by Formula (IIa))

[Formula (IIa)]

(IIa)

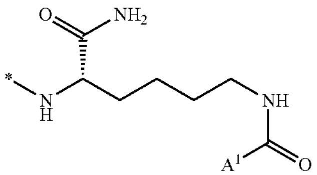

(In Formula (IIa), * denotes a linking moiety, and $A^1$ denotes a $C_8$-$C_{12}$ alkyl group)

[Formula (VI)]

(VI)

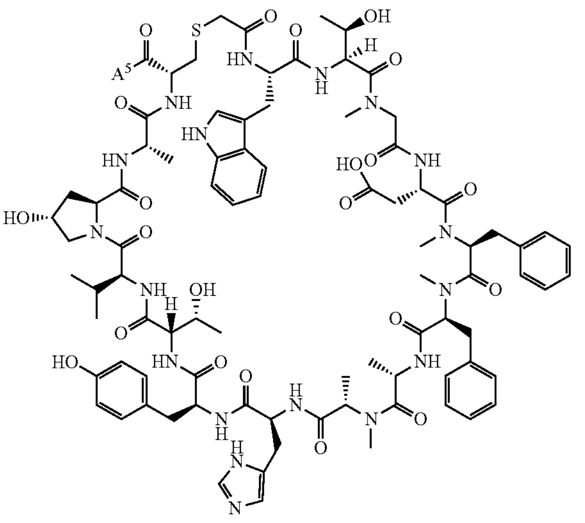

In Formula (VI), Formula $A^5$ denotes a group represented by —$NH_2$ or Formula (I).

6. The hemagglutinin-binding peptide, the pharmaceutically acceptable salt thereof, or the solvate thereof according to claim 3, wherein the hemagglutinin-binding peptide is represented by the following Formula (VII)

[Formula 8(VII)

(VII)

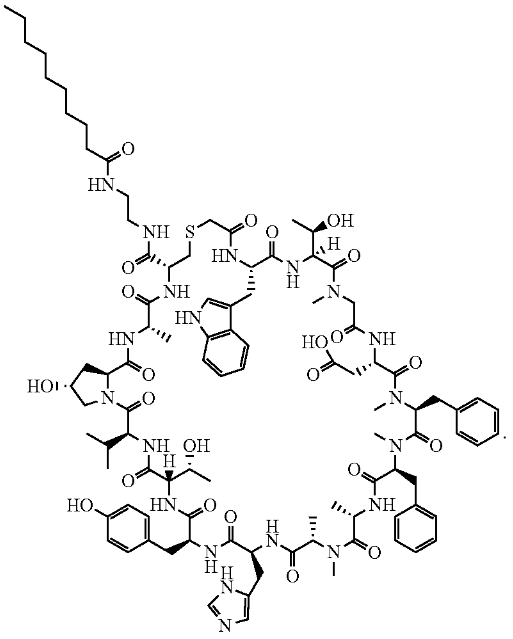

7. A medical drug for prevention of virus infection or for therapy of a virus infectious disease comprising the hemagglutinin-binding peptide, the pharmaceutically acceptable salt thereof, or the solvate thereof according to claim 1.

8. A medical drug for prevention or therapy of influenza comprising the hemagglutinin-binding peptide, the pharmaceutically acceptable salt thereof, or the solvate thereof according to claim 1.

9. A virus detection agent comprising the hemagglutinin-binding peptide, the pharmaceutically acceptable salt thereof, or the solvate thereof according to claim 1.

10. An influenza virus detection agent comprising the hemagglutinin-binding peptide, the pharmaceutically acceptable salt thereof, or the solvate thereof according to claim 1.

11. A kit for virus detection comprising the virus detection agent according to claim 9.

12. A kit for influenza virus detection comprising the influenza virus detection agent according to claim 10.

* * * * *